United States Patent
Napier

(10) Patent No.: US 9,114,317 B1
(45) Date of Patent: Aug. 25, 2015

(54) PATIENT HOSPITAL ROOM SYSTEM FOR PROVIDING COMMUNICATION, EDUCATION AND ENTERTAINMENT

(75) Inventor: David J. Napier, North Little Rock, AR (US)

(73) Assignee: Bluefish, LLC, Little Rock, AR (US)

(*) Notice: Subject to any disclaimer, the term of this patent is extended or adjusted under 35 U.S.C. 154(b) by 2157 days.

(21) Appl. No.: 11/979,248

(22) Filed: Oct. 31, 2007

(51) Int. Cl.
*A63F 9/24* (2006.01)
*A63F 13/00* (2014.01)

(52) U.S. Cl.
CPC ..................... *A63F 13/00* (2013.01)

(58) Field of Classification Search
CPC ....................................... A63F 13/00
USPC ............................... 705/2; 463/25
See application file for complete search history.

(56) References Cited

U.S. PATENT DOCUMENTS

| | | | |
|---|---|---|---|
| 4,151,407 A * | 4/1979 | McBride et al. | 398/106 |
| 5,586,262 A | 12/1996 | Komatsu et al. | |
| 5,867,821 A | 2/1999 | Ballantyne et al. | |
| 5,951,300 A | 9/1999 | Brown | |
| 6,076,166 A | 6/2000 | Moshfeghi et al. | |
| 6,108,634 A | 8/2000 | Podnar et al. | |
| 6,375,469 B1 | 4/2002 | Brown | |
| 6,494,830 B1 * | 12/2002 | Wessel | 600/300 |
| 6,918,769 B2 | 7/2005 | Rink | |
| 6,974,328 B2 | 12/2005 | Aspe et al. | |
| 7,185,282 B1 | 2/2007 | Naidoo et al. | |
| 2001/0037215 A1 | 11/2001 | Sparks | |
| 2002/0010596 A1 | 1/2002 | Matory | |
| 2004/0215490 A1 | 10/2004 | Duchon et al. | |
| 2005/0062238 A1 * | 3/2005 | Broadfield et al. | 280/1 |
| 2005/0086079 A1 | 4/2005 | Graves et al. | |
| 2005/0125255 A1 | 6/2005 | Mockett | |
| 2005/0283385 A1 | 12/2005 | Hunkeler et al. | |
| 2006/0004603 A1 | 1/2006 | Peterka et al. | |
| 2006/0235283 A1 | 10/2006 | Vinarov et al. | |
| 2006/0236247 A1 | 10/2006 | Morita et al. | |
| 2007/0039624 A1 | 2/2007 | Roberts et al. | |
| 2007/0118389 A1 | 5/2007 | Shipon | |
| 2008/0059519 A1 * | 3/2008 | Grifftih | 707/104.1 |

* cited by examiner

*Primary Examiner* — Hiep V Nguyen
(74) *Attorney, Agent, or Firm* — Shlesinger, Arkwright & Garvey LLP

(57) ABSTRACT

A patient hospital room system comprises a room computer uniquely associated with a patient in a hospital room. The room computer is connected to a hospital network including a media server. The room computer is configured to download preselected media files from the media server when a patient is assigned to the room. A touch screen display is operably connected to the room computer and the room computer is configured to enable the touch screen display to function as a remote controller for playing the media files. A game console is operably connected to the room computer. A monitor is connected to the game console. An IR transmitter is connected to the room computer for transmitting commands from the touch screen display to the game console. An IR receiver is operably connected to the game console for receiving the commands from the IR transmitter. The room computer and the game console are configured such that the preselected media files are playable from the room computer and displayable on the touch screen or the monitor.

25 Claims, 31 Drawing Sheets

PATIENT HOSPITAL ROOM SYSTEM FOR PROVIDING COMMUNICATION, EDUCATION AND ENTERTAINMENT

FIELD OF THE INVENTION

The present invention relates generally to a patient hospital room system for providing communication, education and entertainment.

BACKGROUND OF THE INVENTION

A prolonged hospital stay can be an isolating event for a child who has to leave behind friends, families, and schools. This is more evident when a hospital is several hours away from the patient's home. For young people, being removed from everyday contact with peers and families is a great challenge. The phone can help only so much. Adolescents are completely 'hooked up'-to the Internet, to gaming, to their schools.

Typical patient rooms are equipped with a television, a bedside monitor, and a nurse call system; several gaming systems and computers were shared among the rooms. A TV bolted to the ceiling is the extent of the entertainment choices in a typical hospital. When a patient or family member requests a gaming system or a computer, a nurse has to find one that wasn't in use, check it out to the patient, and roll it into the room on a cart. Because of the limited supply, patients often have to wait hours for the equipment and are allowed only one hour of use at a time.

Patients with cystic fibrosis are isolated from other patients because of the potential for fatal cross-infection. Consequently, one of the biggest difficulties with the shared gaming and computer systems is compliance with infection control. Each piece of electronic equipment, including monitors, keyboards, and handheld controllers, has to be disinfected each time it is moved from one patient's room to another. This is not simply a quick wipe. Where cross-infection of one resistant organism from one patient to another can be fatal, the equipment must be thoroughly cleaned.

Providing Internet access for families who needed it to stay connected to their jobs or to research information about their child's condition is also difficult to provide, if at all available. Often, parents have to leave the child's room to obtain an Internet connection when parents don't generally want to leave the child's bedside to explore more information about the child's diagnosis and care, and what they can do to help. Additionally, there is a great need for children and often family members to use the Internet to keep up with schoolwork.

SUMMARY OF THE INVENTION

The invention is directed to a patient hospital room system comprising a room computer uniquely associated with a patient in a hospital room. The room computer is connected to a hospital network including a media server. The room computer is configured to download preselected media files from the media server when a patient is assigned to the room. A touch screen display is operably connected to the room computer and the room computer is configured to enable the touch screen display to function as a remote controller for playing the media files. A game console is operably connected to the room computer. A monitor is connected to the game console. An IR transmitter is connected to the room computer for transmitting commands from the touch screen display to the game console. An IR receiver is operably connected to the game console for receiving the commands from the IR transmitter. The room computer and the game console are configured such that the preselected media files are playable from the room computer and displayable on the touch screen or the monitor.

The invention is further directed to a patient hospital room system, comprising a room computer uniquely associated with a patient in a hospital room. The room computer is connected to a hospital network including a database server. The room computer is configured to periodically check for and load setting options stored in the database server. A touch screen display is operably connected to the room computer. The room computer is configured to enable the touch screen display to function as a remote controller. A game console is operably connected to the room computer. A monitor is connected to the game console. An IR transmitter is connected to the room computer for transmitting commands from the touch screen display to the game console. An IR receiver is operably connected to the game console for receiving the commands from the IR transmitter.

The invention is still further directed to a patient hospital room system, comprising a room computer uniquely associated with a patient in a hospital room. A touch screen display is operably connected to the room computer. The touch screen display includes a plurality of buttons, each one corresponding to a command when pressed. The room computer is configured to create a text file corresponding to a button pressed on the touch screen display, read the text file and initiate the command. A game console is operably connected to the room computer. A monitor is connected to the game console. An IR transmitter is connected to the room computer for transmitting the command from the touch screen display to the game console. An IR receiver is operably connected to the game console for receiving the commands from the IR transmitter.

DETAILED DESCRIPTION OF THE INVENTION

Figure 1:
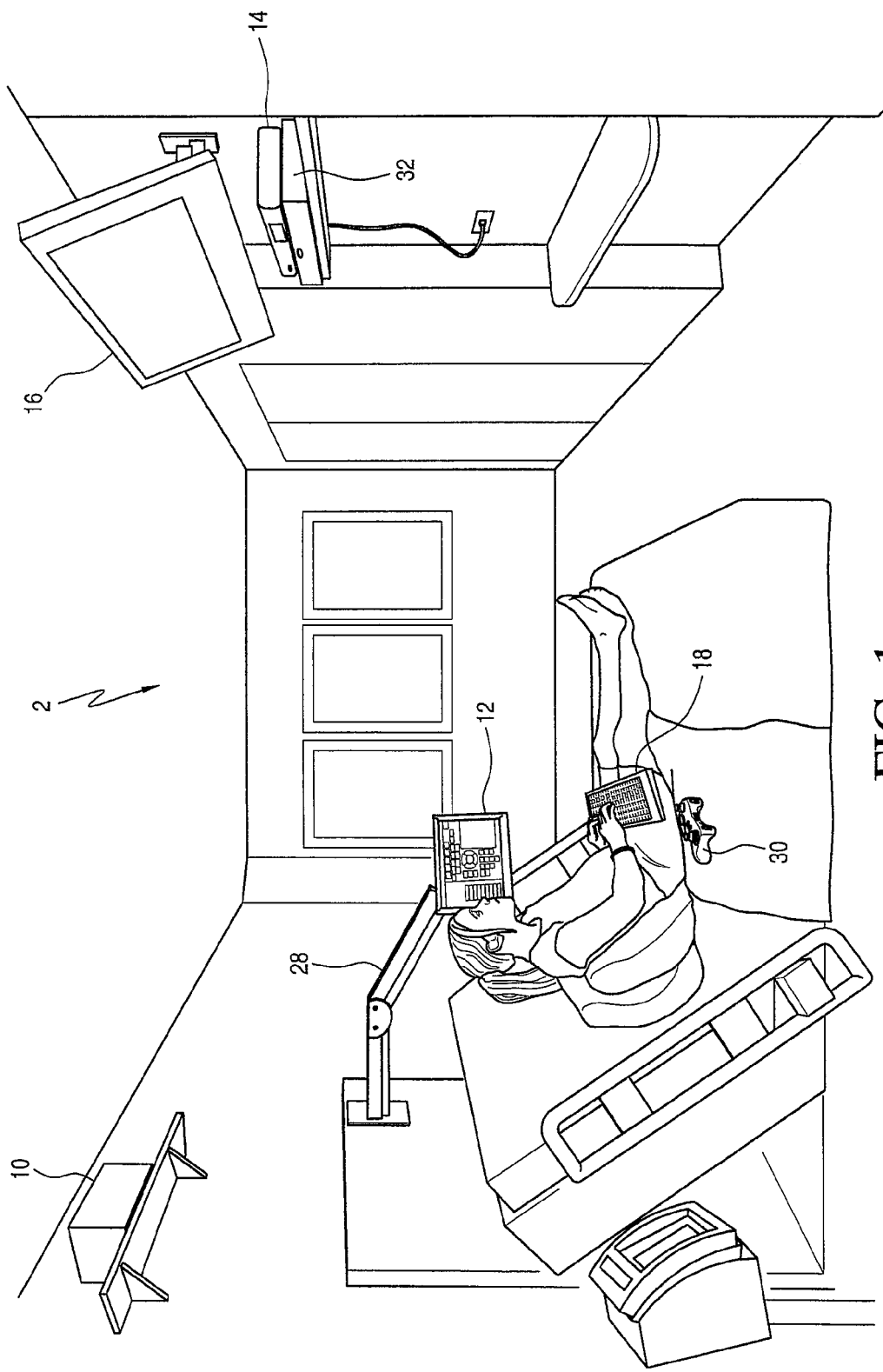
FIG. 1 is a perspective view of a patient hospital room equipped with an embodiment of a system made in accordance with the present invention.
Figure 2:
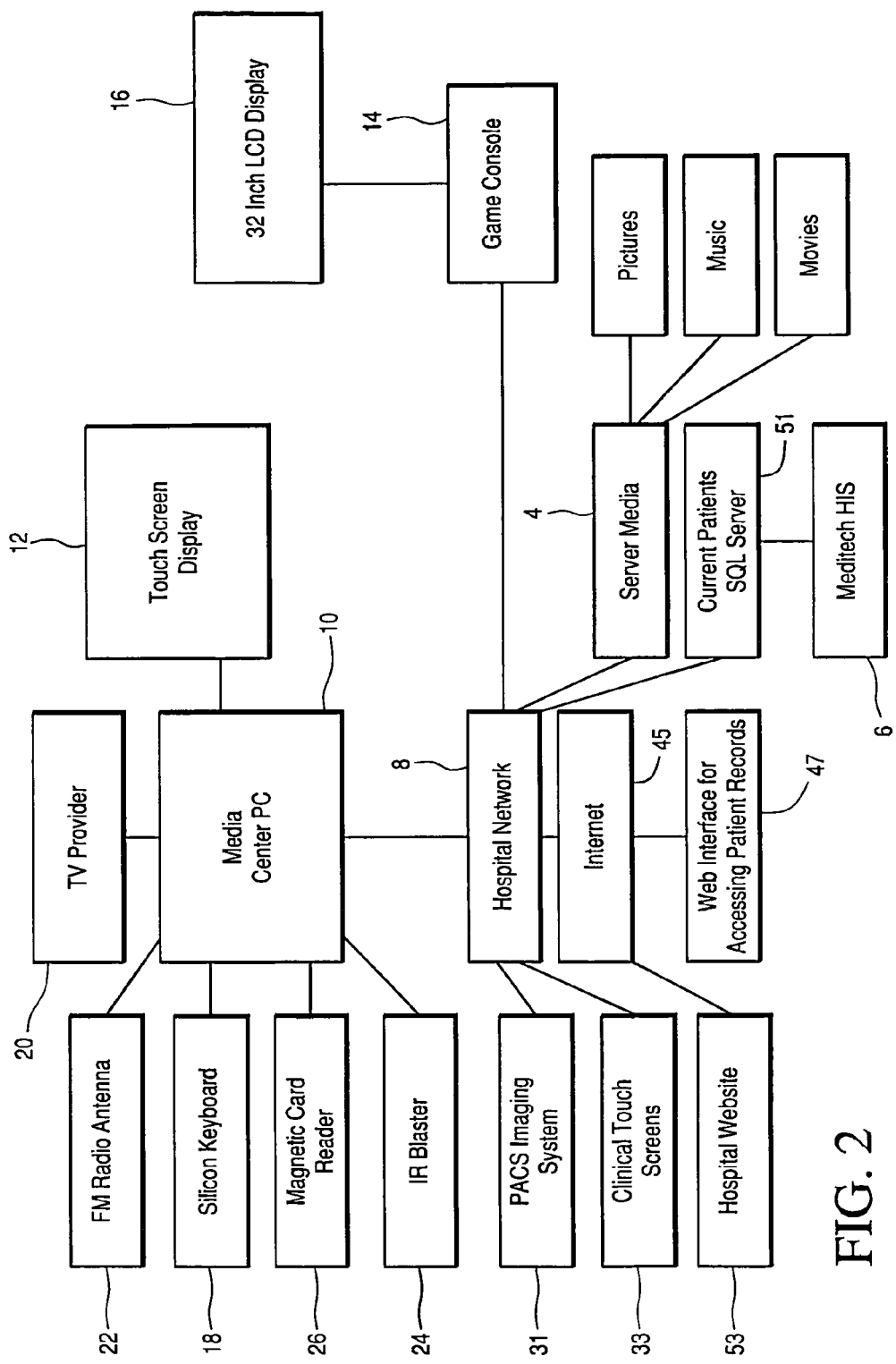
FIG. 2 is a functional block diagram of an embodiment of a patient hospital room system made in accordance with the present invention.

An embodiment of a patient hospital room system 2 in accordance with the present invention is disclosed in FIGS. 1 and 2. The system 2 is connected to a central media server 4 and a patients medical records system 6, such as the commercially available Meditech Hospital Information System provided by Medical Information Technology, Inc., through a hospital network 8.

The system 2 is disposed within the room and comprises a PC 10 connected to the hospital network 8, a touch screen display 12 connected to the PC 10, a game console 14 connected to the PC 10 via the hospital network 8, and a large screen display 16 connected to the game console 14. The PC 10 is uniquely associated with a patient in the hospital room. A sealed silicon keyboard 18 is connected to the PC 10. A TV source 20, such as cable TV, is connected to the PC 10 for providing television programs. A radio source 22, such as a FM antenna, is connected to the PC 10 for providing radio programs. An IR blaster 24, which is an IR transmitter designed to transmit standard remote control commands, is connected to the PC 10 to communicate viewing requests from the touch screen 12 through the PC 10 to the game console 14 and the monitor 16. A card reader 26, such as for reading a magnetic card, is connected to the PC 10.

The PC 10 is installed on the wall behind and above the headboard of the hospital bed. The touch-screen display 12 is attached to a swing arm 28 mounted to a headboard. The large screen display 16 is mounted high on the wall in front of the hospital bed. The game console 14 is mounted on a shelf below the display 16. A wireless game controller 30 is used to control the game console 14. The PC 10 is configured to control the functions of the various components of the system as described herein.

The embodiment disclosed uses a Microsoft XBox 360 (trademark) system for the game console 14. The PC 10 is preferably a media center running on Microsoft Windows XP Professional.

The patient can access TV programs, music, photos, movies, and other content through the game console 14 and view them on the display 16 on the wall in front of the hospital bed.

Figure 3:
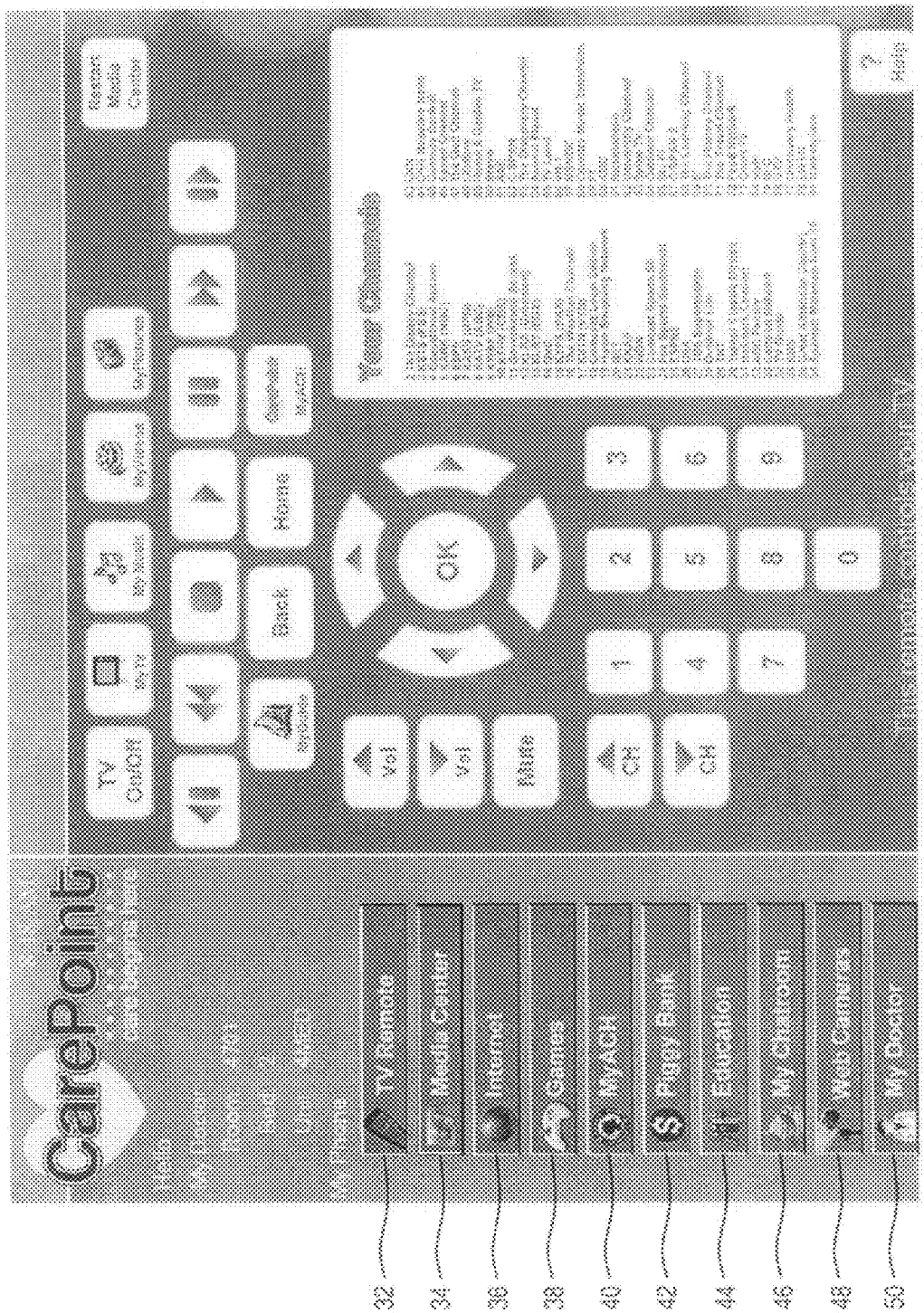
FIG. 3 is a sample screenshot of a touch screen display showing a number of provided features and TV remote control functions.

Referring to FIG. 3, the touch screen display 12 provides multiple modes of functionality. The touch screen 12 functions as a "Main Menu" for the system 2, allowing a patient to choose among the functions of the system, namely, TV Remote 32, Media Center 34, Internet Access 36, Games 38, Hospital Intranet 40, "Piggy Bank" Account 42 (fundable debit-type card), Diagnosis-Specific Educational Videos 44, Chat Room 46, Web Cameras (hospital based) 48 and My Doctor 50, (a method to leave a message for the doctor). The TV remote function includes all the standard functions, as shown in FIG. 3.

The replacement of the typical button-driven remote control with a touch screen display 12 provides a level of sanitation not available with prior art systems. Each bedside system needs to be sterilized before a new patient is moved into a room. Components of the system 2 advantageously have minimal cracks and crevices so that they are easy to wipe clean. The touch screen display 12 can be sprayed with a germicide and wiped clean. The prior art remotes often have to be replaced after each patient, particularly if the patient is in isolation and considered highly-susceptible to infection. A completely sealed silicon "keyless" keyboard is also used.

The IR blaster 24 allows the touch screen 12 to communicate with the television monitor 16, allowing patients to turn the TV on and off, adjust the volume, scroll up and down through channels and turn the game console on and off. When the user presses a button on the touch screen 12, a command is sent to the computer 10, which then sends the command to the IR blaster 24 to an IR receiver 32 below the display 16, that in turn sends the command to the game console 8. Accordingly, the touch screen 12 enables the user to access TV programs, movies on demand, games, and music; open a Web browser; start a chat session; or send e-mail using the display 16.

The system 2 allows the patient the option to display most materials on either the touch screen display 12 or the display 16 and can even allow both monitors to display different materials, simultaneously, allowing a parent to utilize (for example) the touch screen 12 to access an email account while the patient watches a movie or TV show on the monitor 16.

The video content resides on the centralized media server 4. When a patient requests a video or music file, that file is transferred to the PC 10 in the room and played back from there, instead of being streamed from the central media server 4. The file can be transferred in seconds, which greatly reduces the load on the hospital network 8, compared to 280 rooms all wanting to stream a media file directly from the centralized server 4. TV channels from the TV source 20, likewise, feed directly from the PC 10 in the room. Whether any content is displayed on the touch screen display 12 or the monitor 16 is strictly a matter of choice for the patient and lessens the load on the hospital network 8, since the content is already on the PC 10 in the room. The PC 10 is also preloaded with "favorites", based on a patient's or guardian's previous choices. The system monitors the TV programs and movies that the patient watches and pre-loads content to the PC 10 in the room for subsequent visits.

Digital content, including movies, music, and educational videos, is stored in the server 4. In the time it takes for a patient to enter the room after check-in, the system retrieves patient information, such as age and sex, and automatically downloads from the server 4 appropriate content to the PC 10 associated with the room. The system is, thus, advantageously "de-centralized", utilizing the existing hospital network infrastructure to move media content from a centrally-located server to the PC 10 in the patient's room for playback, thereby eliminating excessive traffic over the network and bypassing the need to establish a standalone network to handle access to the various media content.

The game console 8 provides full gaming functions, but also serves to route most video functions to the display 16. The display 16 is primarily for viewing movies, educational videos and games, controlled by the bedside touch screen display 12. The system utilizes the game console 8 not only for its gaming purpose, but also as an extension of the PC 10, allowing the game console 14 to display content from the PC 10.

Figure 4:
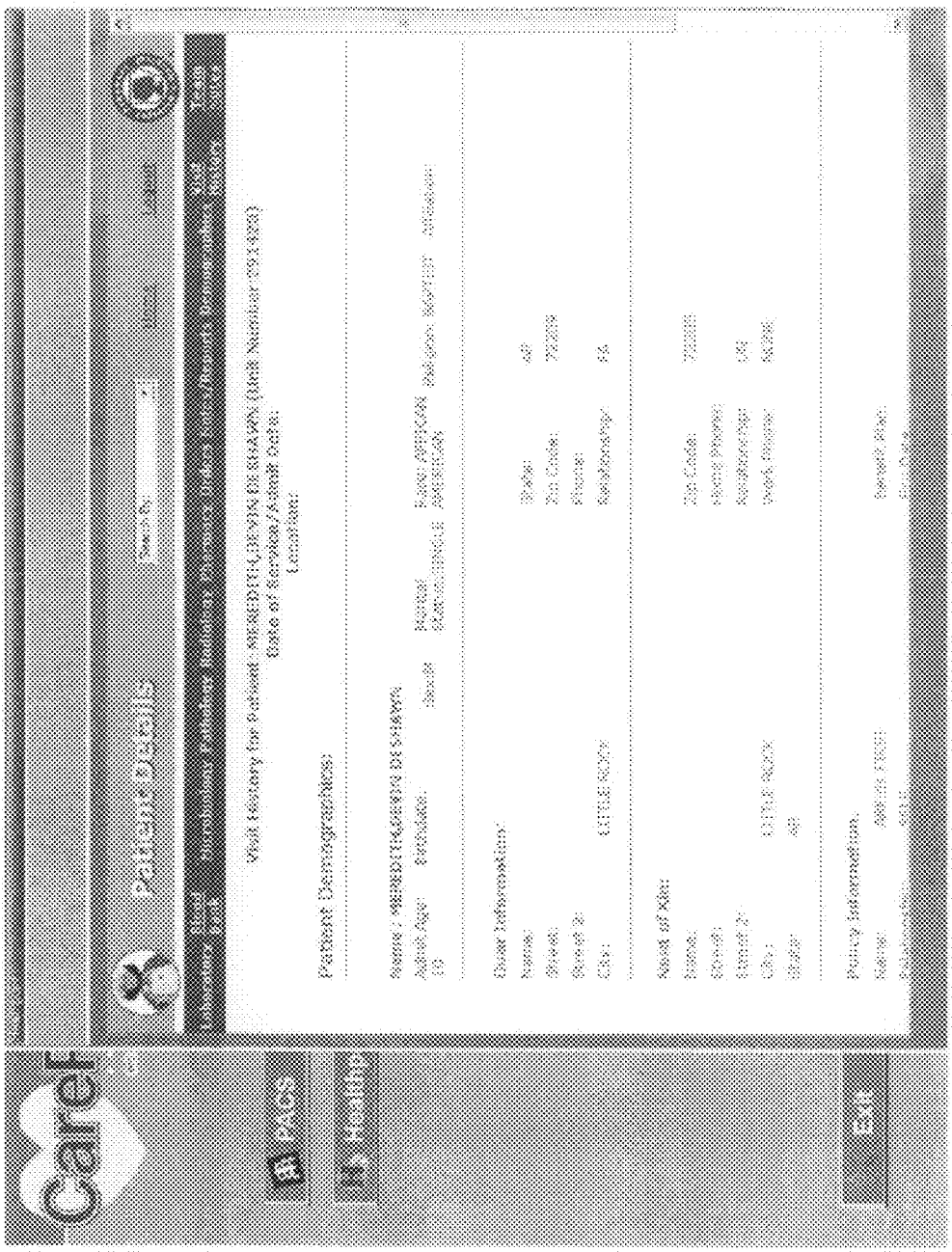
FIG. 4 is a sample screenshot of a display showing a patient's medical information accessible through a bedside touch screen display.
Figure 5:
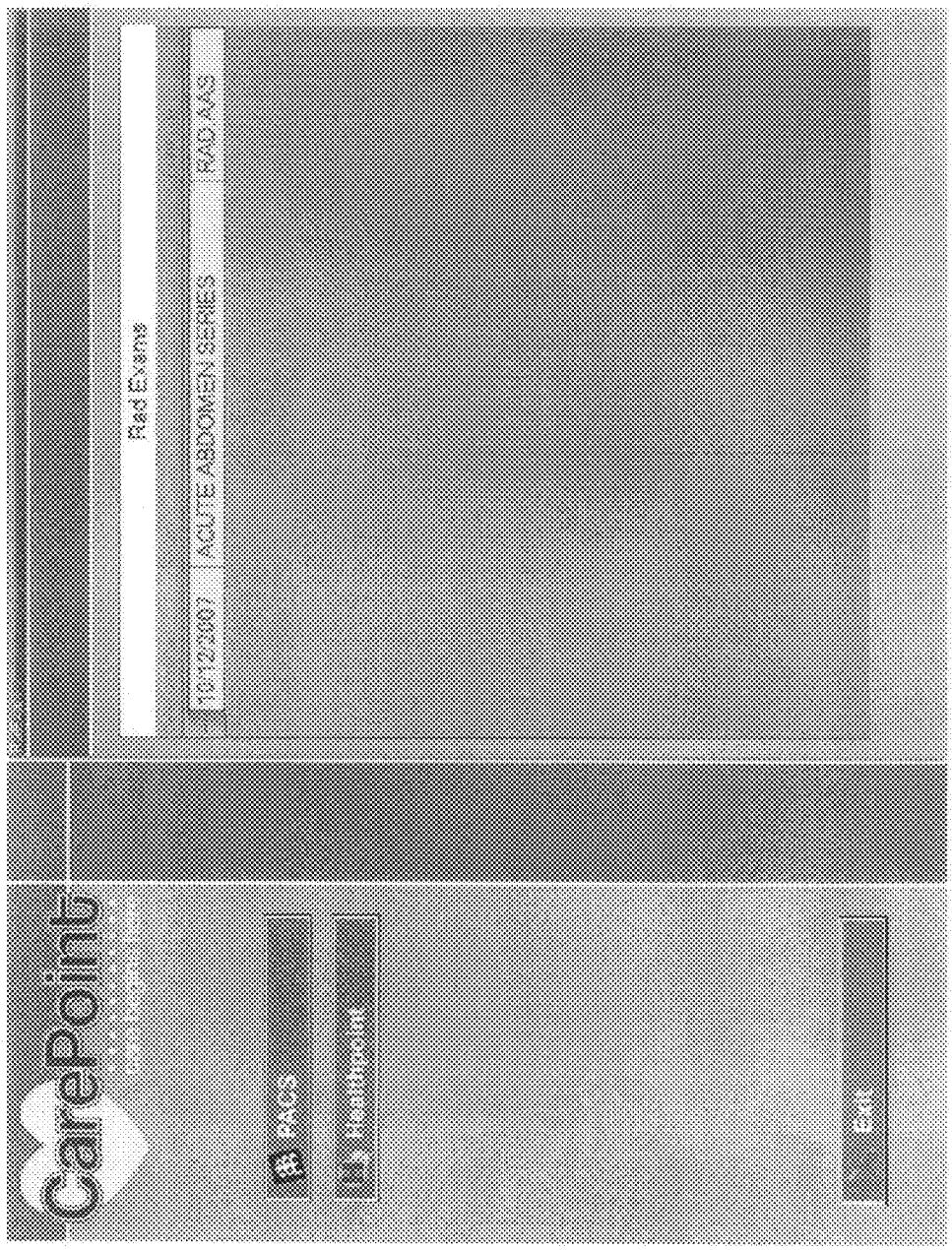
FIG. 5 is a sample screenshot of a display showing a patient's radiological pictures available through a bedside touch screen display.

The touch screen display 12 also functions as a control center for a doctor, who gains access to the patient's medical information after swiping his ID card through the card reader 26 in the room to read identity information stored on a hospital identification card. Access to the medical records is limited to doctors and nurses who have been delegated responsibility for that patient. A database server 51, for example running on Microsoft SQL server software, verifies authorized access via data from the Meditech hospital information system records 6, based on Social Security number, and presents the medical team member with a display on the touch screen 12, as shown in FIG. 4, through Web interface 47, allowing the doctor to select the type of information desired to be displayed, such as test results, radiology scans, etc. Requests for that information are passed to the hospital information systems and delivered to the display 12 via the existing hospital network 8. Accordingly, bedside access to patient records stored in the hospital information system 6 is provided, such as lab results and x ray or digital radiology images. The laboratory results and images are displayed on the touch screen 12 for the patient's viewing. An example of a screenshot showing access to a patient's radiology pictures is shown in FIG. 5, using a commercially available Picture Archiving and Communications System (PACS) 31 for displaying a medical record of the radiological or x-ray type.

Prior to admission, if the patient has been scheduled for a hospital visit, the patient can use a web-based portal 53 (access-controlled by a secure username and password combination) through a remote PC to upload music files, photographs to the central media server 4, and change certain access settings for the system (hours of operation, movie limits, etc). Patient-specific information about these choices is stored in a SQL Server-based table in the server 51 for access by the system.

The system 2 is activated when a patient is admitted to the hospital and assigned to a room. Because the system is designed to constantly monitor the current patient database in the underlying Meditech hospital information system, it knows when the patient has been admitted. As soon as the system recognizes that the patient has been assigned to a specific room, it acknowledges the patient's age and gender and begins loading appropriate audio and video files to the PC 10 in the patient's room. The system also loads all of the material the patient may have uploaded via the website portal 53. The system utilizes the hospital's existing 100 mbps network infrastructure to transfer the material from the media server 4 to the PC 10. This decentralized design, that preloads material, lowers the demand for network resources, compared to a fully-centralized system that utilizes the network infrastructure to "stream" material on-demand directly from a centralized server.

The server 51 monitors the Current Patient Database and creates a table listing all changes in hospital room assignments (admissions, discharges, and transfers). The table is updated every few minutes. A table listing of "tasks" based on the patient information and the room assignment is generated. The PC 10 is configured to survey the table periodically (utilizing the existing hospital network infrastructure), looking for operations or tasks specified for itself. These operations may include commands to transfer specified video and audio files to the PC 10, set access parameters specified earlier via the web-based portal and provide access to patient medical records. The PC 10 polls the server 4, asking to be notified of any changes in files or access parameters. When the PC 10 is notified of the change, it performs the requested action.

The system uses "file watching" technology, available from Microsoft Visual Studio software, as the method of communication between the various hardware parts of the system, such as the PC 10, the game console 14 and the media server 4. The file watching technology delivers control commands from the touch screen 12 to the PC 10 and the game console 14 by writing text-based commands to a shared file that is monitored by the system. These text-based commands are converted into standard keyboard commands for control of the display on the monitor 16 via the game console 14. The file watching technology is also used as a bridge around the hospital network firewall to allow control of the system via the Web-Based portal 53. When a command is issued via the portal, a small text file is written to the server 51.

The file watcher is included as part of Microsoft Visual Studio software and forms the basis for many of the commands to be interpreted by the various pieces of hardware and then acted upon. When a patient, for example, touches the "music" button on the touch screen display 12, the system writes a small text file to the hard drive of the media center computer 10. That file contains the command to display the music library. The file watcher watches for any such files, looks at them, and passes the command on to the system. Hundreds of those files are written and read daily, each within milliseconds, allowing the response on the screen to be almost instantaneous.

Figure 6:
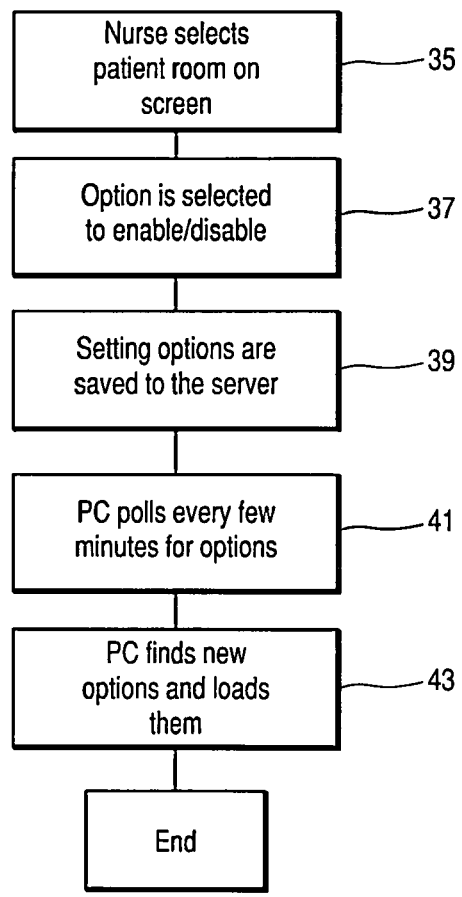
FIG. 6 is a flowchart for selecting options for a patient's hospital room system.

Nurses have full control over each bedside system. From a computer at the nurse's station, system components can be turned on or off, most commonly for the purpose of imposing a gaming curfew. Referring to FIG. 6, a nurse may access a clinical touch screen 33 mounted outside the patient's room to change options for a patient. When the nurse selects a patient room at 35, the system displays the current list of options that can be enabled or disabled at 37. The chosen selections are saved to the server 51 at 39. The PC 10 in each room polls the server every few minutes at 41 for updated settings. If the PC finds new settings, those updated settings are loaded at 43.

The Web portal 53 uses the Microsoft ASP.NET software. The portal 53 allows family members and friends to interact with the patient from outside the hospital, such as those people who are not in the room, the other parent at work, or an aunt several states away, by connecting to the Internet 45. Through the portal, users are able to share pictures and music files or conduct chat sessions. The portal includes parental controls. The portal also allows patients and their families to watch educational videos and sign up for the hospital's education curriculum from home. The Web portal 53 enables patients and family to interact with their friends outside the hospital through pictures, messages, video, and chat.

Figure 7:
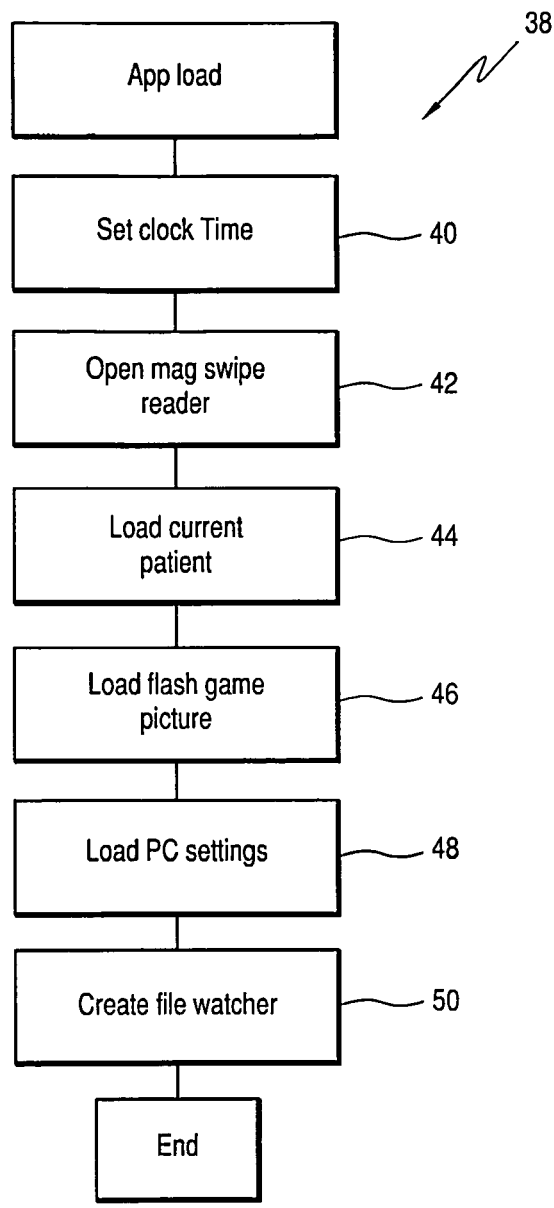
FIG. 7 is a flowchart showing the steps the system goes through when the system initially starts.

Referring to FIG. 7, an application loader flowchart 38 is disclosed, showing the steps the system goes through when it initially starts. The system creates a clock time on the screen 12 at 40, based on the PC time. The magnetic stripe reader 26 is initialized at 42 to open the port that the reader is attached to, to assure that it will be accessible, when needed. The next step is for the system to check the database in the server 51 at 44 to find the patient information in the Current Patient Database and then displays that information on the screen 12. The system then checks for the available games and loads the paths to those games at 46. By keeping this list in a database, the list of games available can be dynamically modified and have the updated list automatically presented every time the system starts up. The system then loads the settings for the system at 48 (all of the menu options displayed on the screen 12). This allows selections to be locked out by operators who have access to the database. The system then creates a File Watcher at 50 (a function of the Microsoft Visual Studio Programming System). The File Watcher monitors the chat system for any new traffic. This eliminates the need for constant "polling" of the server to monitor the chat process. In essence, the File Watcher notifies the system of new chat traffic and assigns it to the correct patient, or rejects it, based on parameters set by the user.

Figure 8:
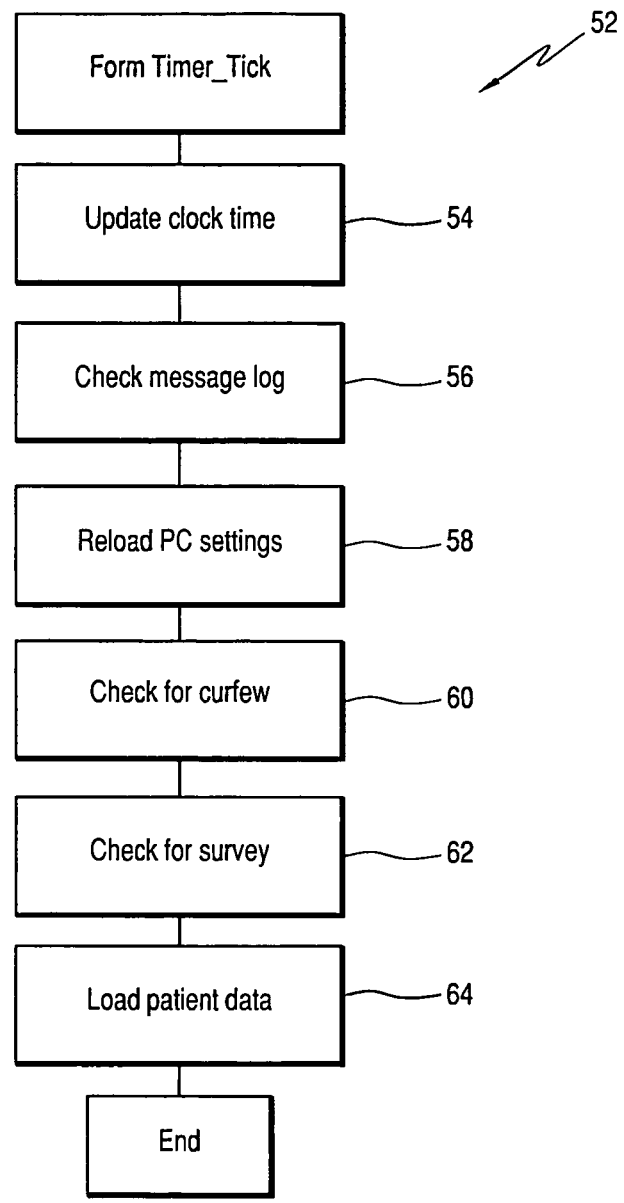
FIG. 8 is a flowchart of a process that runs constantly in the background to assure current information is displayed on the touch screen.

Referring to FIG. 8, a form timer flowchart 52 is disclosed. The form timer runs constantly in the background to assure current information is displayed on the touch screen 12. The system updates the current clock time at 54, based on the PC Lime. Then, the system checks for any new messages for the current patient at 56 and displays an on-screen notification of new messages. If there are new messages, the system creates an onscreen button to allow the patient to access those messages. A similar notification is displayed on the TV screen 16, via the PC 10. The system then checks the server 51 and reloads system settings at 58, to assure the current access rights are utilized. The system then checks the server 51 for any curfew times at 60 that may have been entered by a parent (via the Web Portal) or a nurse. If a curfew time in scheduled within five minutes, the system will display a message on the touch screen 12, notifying the patient that the system will be shut down. The system then begins an on-screen countdown to the shutdown time. At that point, it displays a message counting down to the next time that the system will be available. The system then checks the server 51 at 62 to see if there is a survey for the patient to take. If there is, the system creates a button on the touch screen 12 to allow the patient access to the survey. The surveys are used, for example, to gauge patient satisfaction with their stay in the hospital. Finally, the system checks and reloads the current patient status at 64, from the Current Patient Database.

Figure 9:
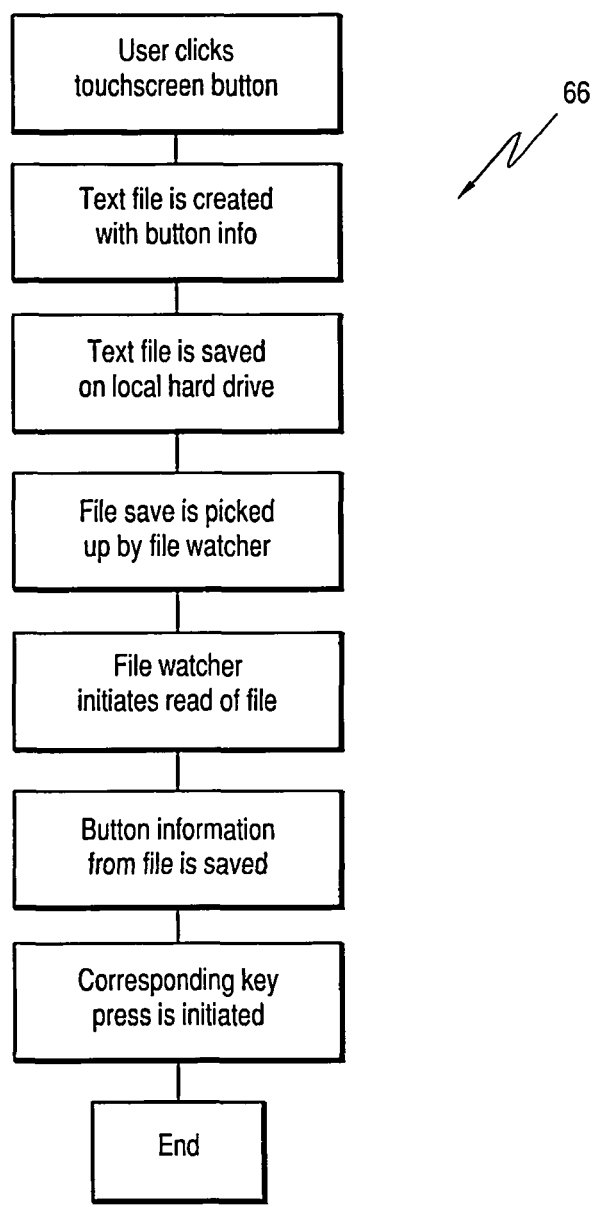
FIG. 9 is a flowchart of a process that translates all of the touch screen actions into functions on the room computer.

Referring to FIG. 9, a file watcher flowchart 66 is disclosed. The file watcher translates all of the touch screen actions into functions on the PC 10. For example, when a patient touches the "down" arrow to move the cursor on the menu displayed on the monitor 12, the system writes a small text file to the PC 10. The file watcher that is running on the PC 10 sees the new file, reads the file and processes the command, utilizing the Microsoft API to translate the command. For example, if the "down" arrow is pressed on the touch screen 12, the system writes a text file containing the Microsoft API command to tell the program to move the cursor down on the screen, just as if the down arrow had been pressed on a keyboard.

Figure 10:
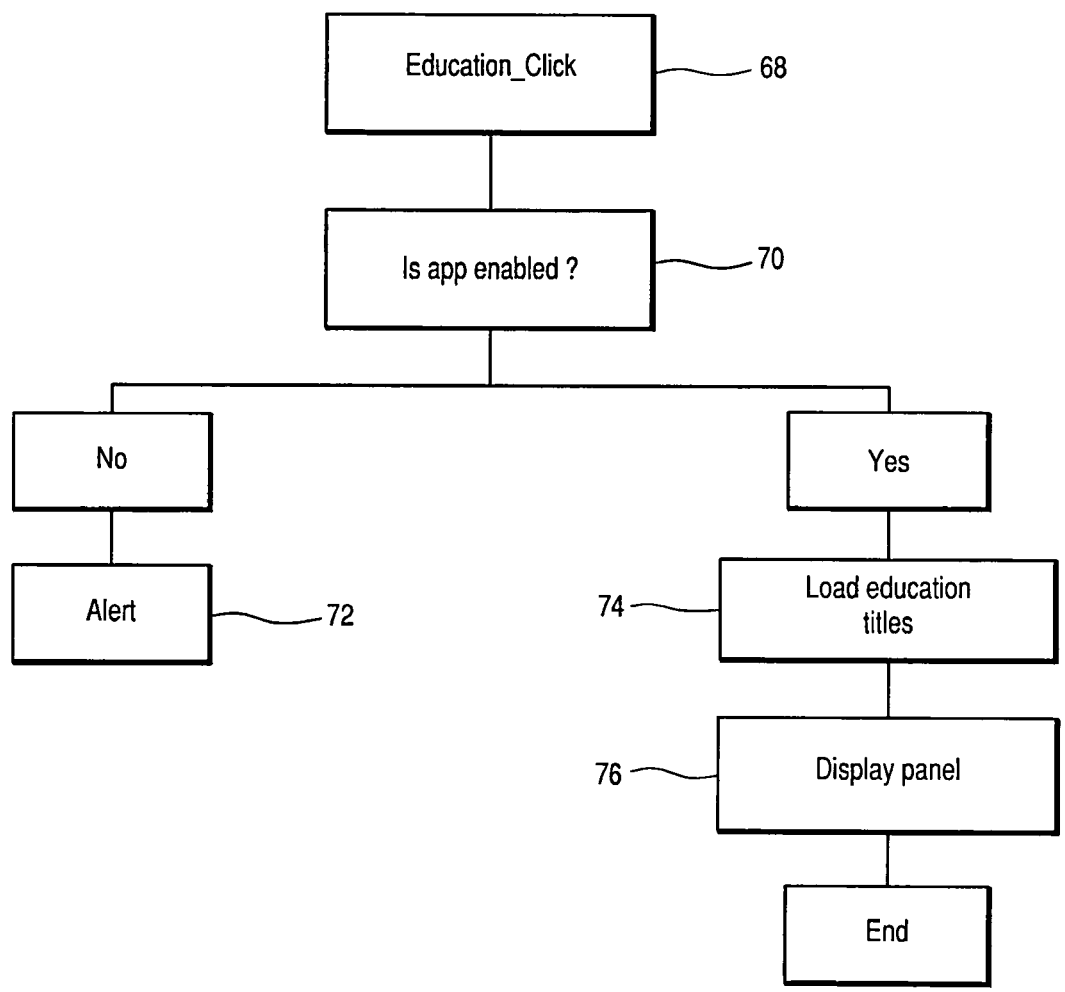
FIG. 10 is a flowchart showing the process when a patient presses the education button on the touch screen display.
Figure 11:
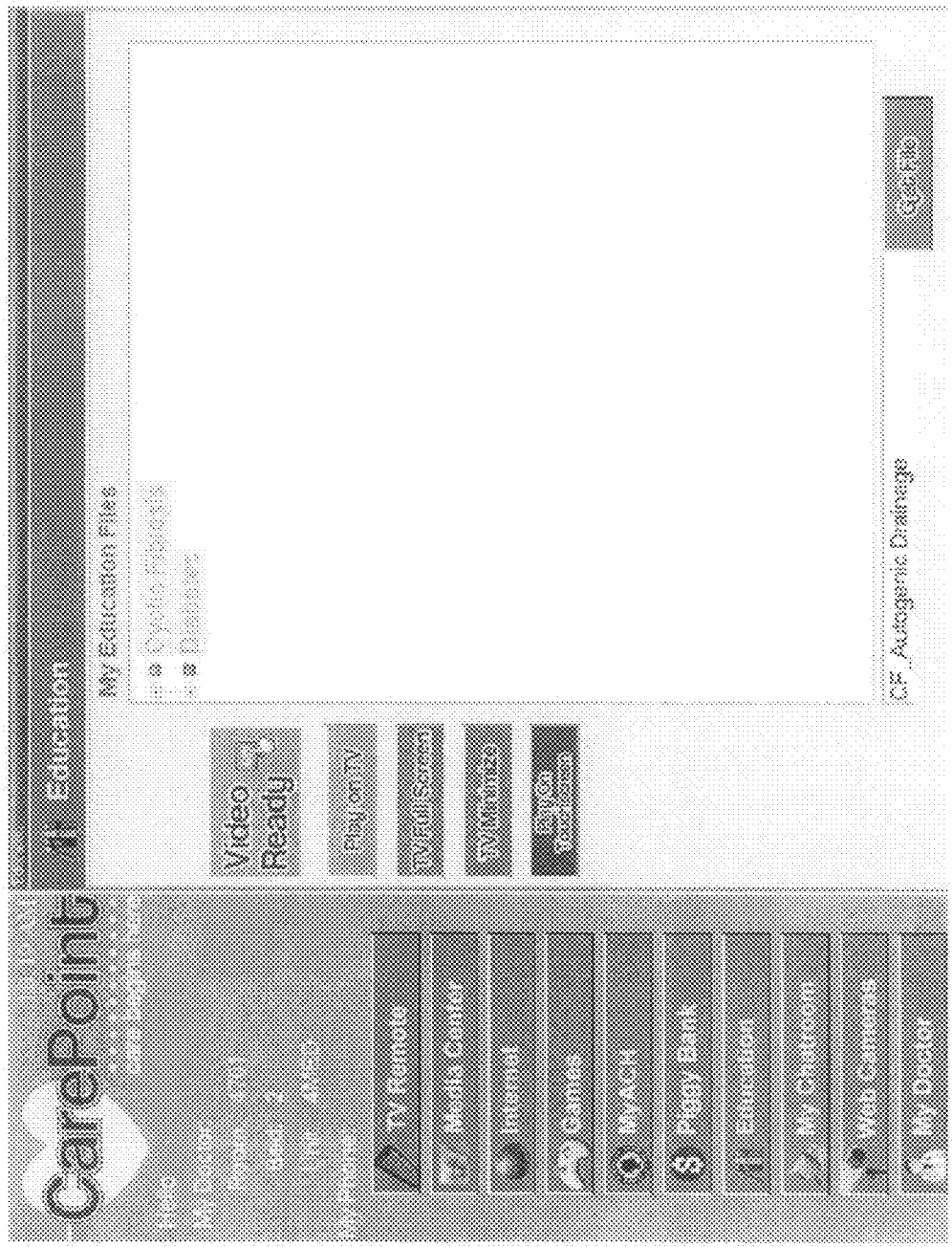
FIGS. 11-13 are sample screenshots of a display when a patient presses the "Education" button on the touch screen display showing diagnosis specific videos available to the patient.
Figure 12:
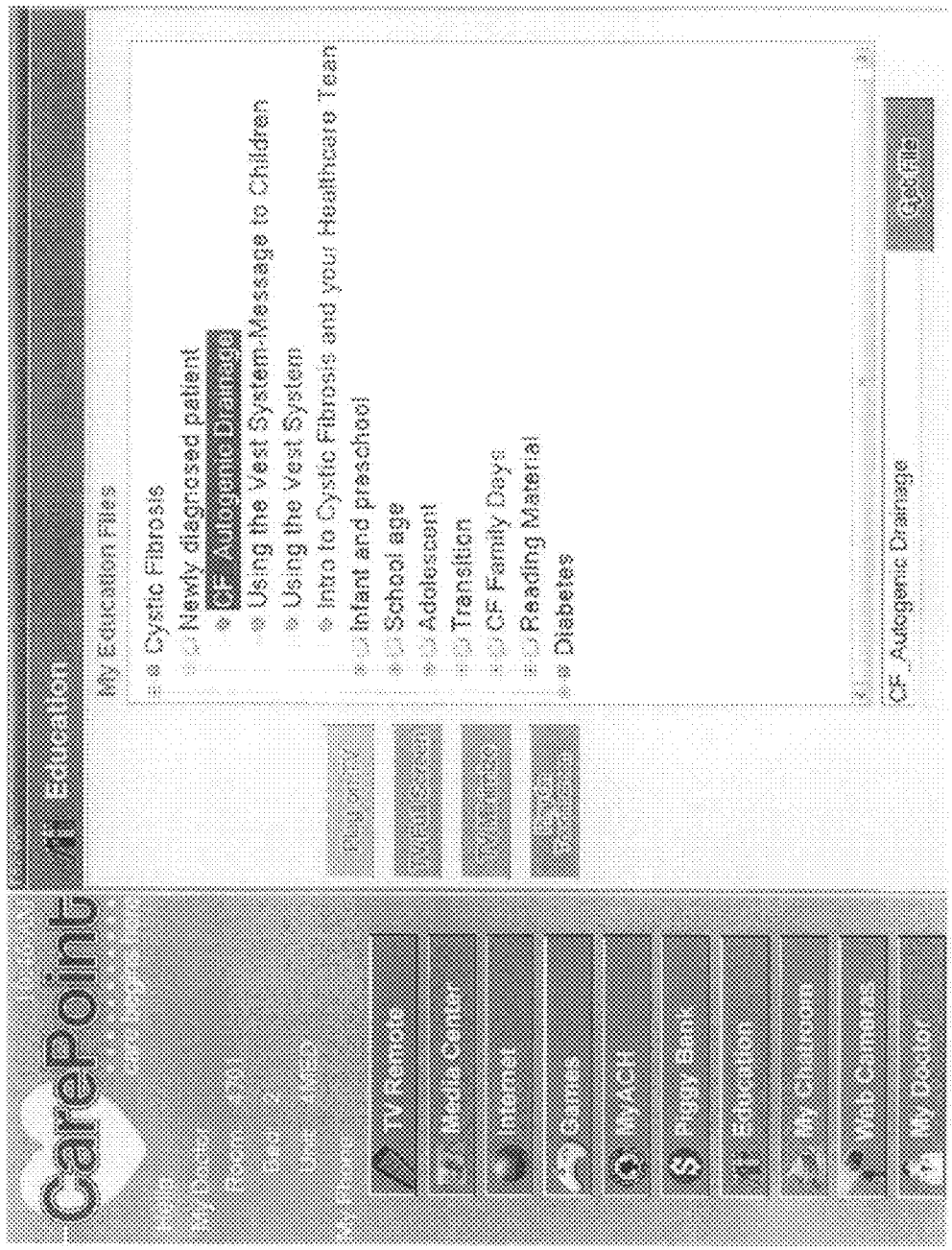
Figure 13:
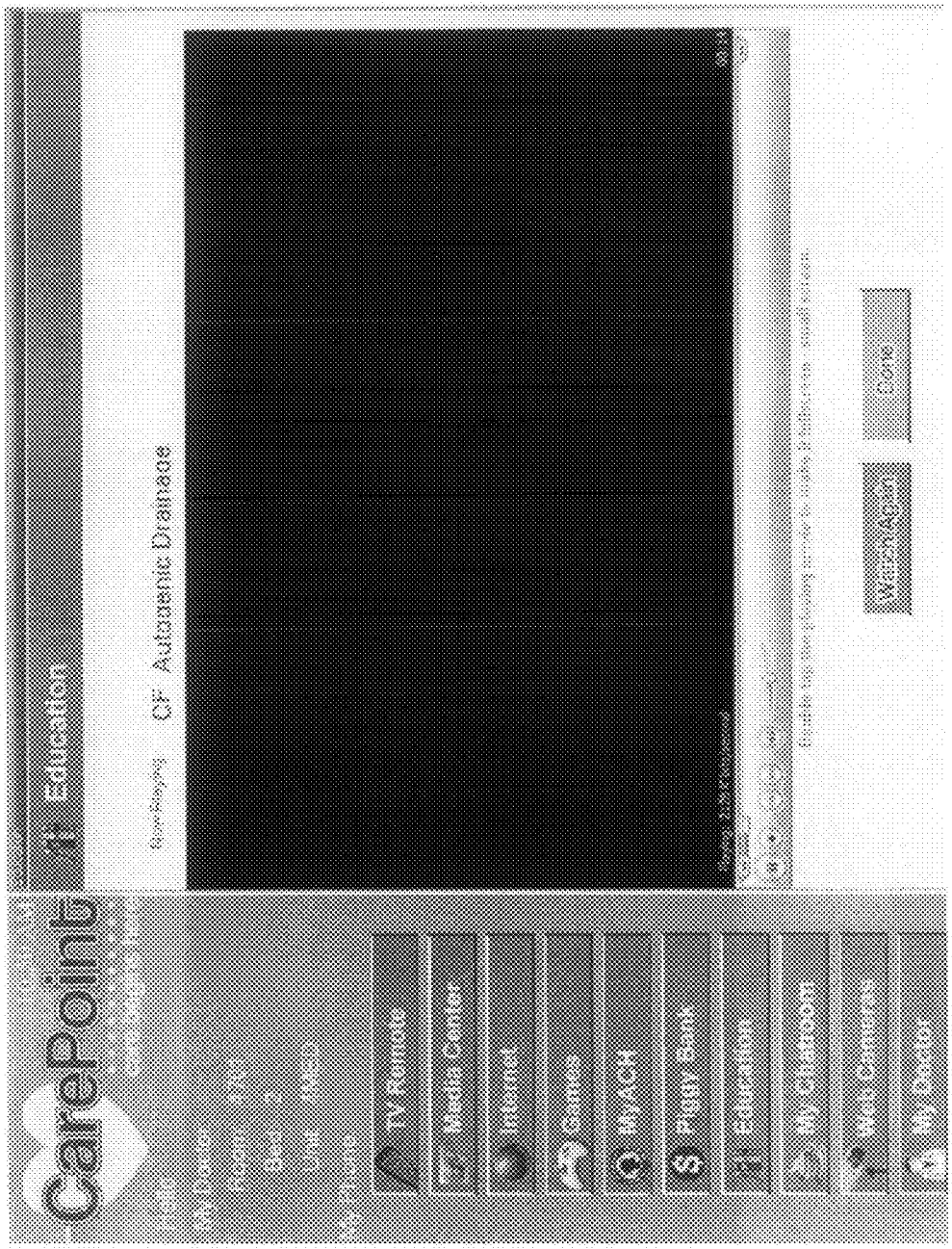

Referring to FIG. 10, when the "Education" button 44 on the touch screen 12 is pressed at 68, the system checks the PC settings at 70 to verify that a patient is assigned to the room. If there is no patient assigned, the system displays a message that the system is locked at 72. If there is a patient in the room, the system looks at the database in the server 51 to load the location of all educational material at 74 into a tree view display at 76 on the touch screen 12. This allows the patient to select a video, based on diagnosis. Examples of screenshot displays are shown in FIGS. 11-13. By touching, for example, "Cystic Fibrosis" on the screen, the system will display a list of all cystic fibrosis-specific videos, based on specifications in the database in the server 51. The video may then viewed on the touch screen display 12, as shown in FIG. 13, or on the large screen display 16.

Figure 14:
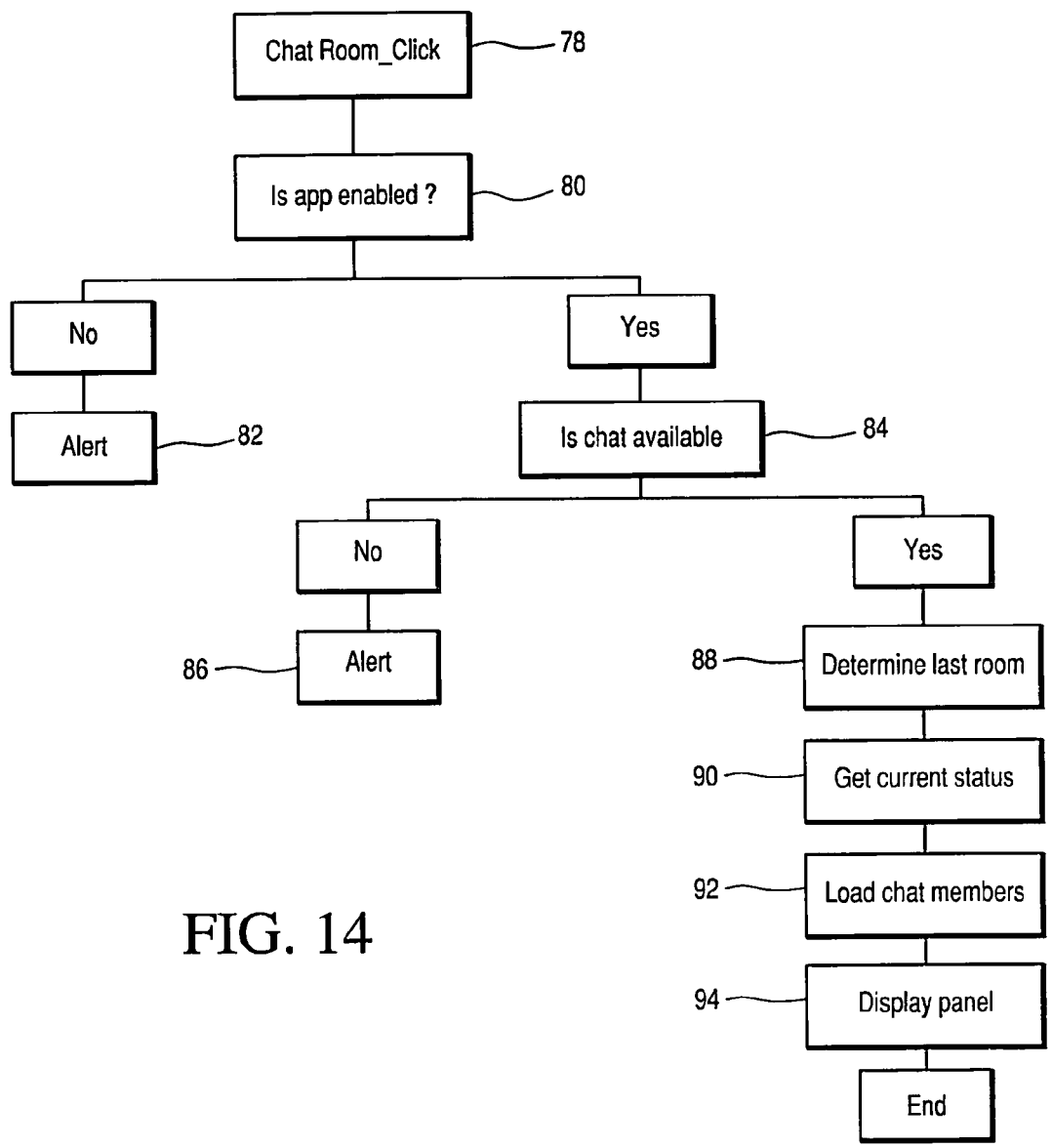
FIG. 14 is a flowchart showing the process when the "My Chatroom" button on the touch screen display is pressed.
Figure 15:
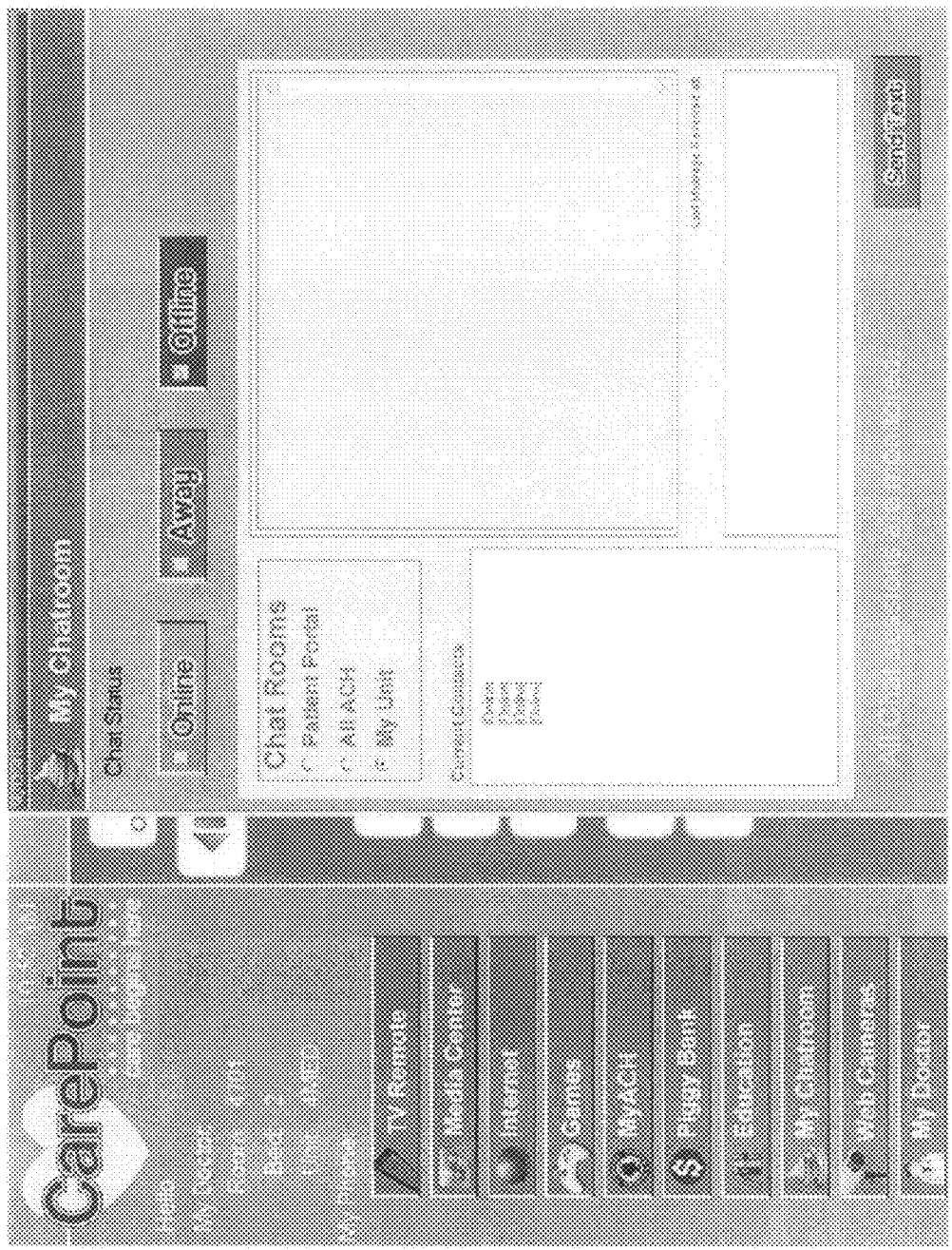
FIG. 15 is a sample screenshot of a display when the "My Chatroom" button on the touch screen display is pressed.
Figure 16:
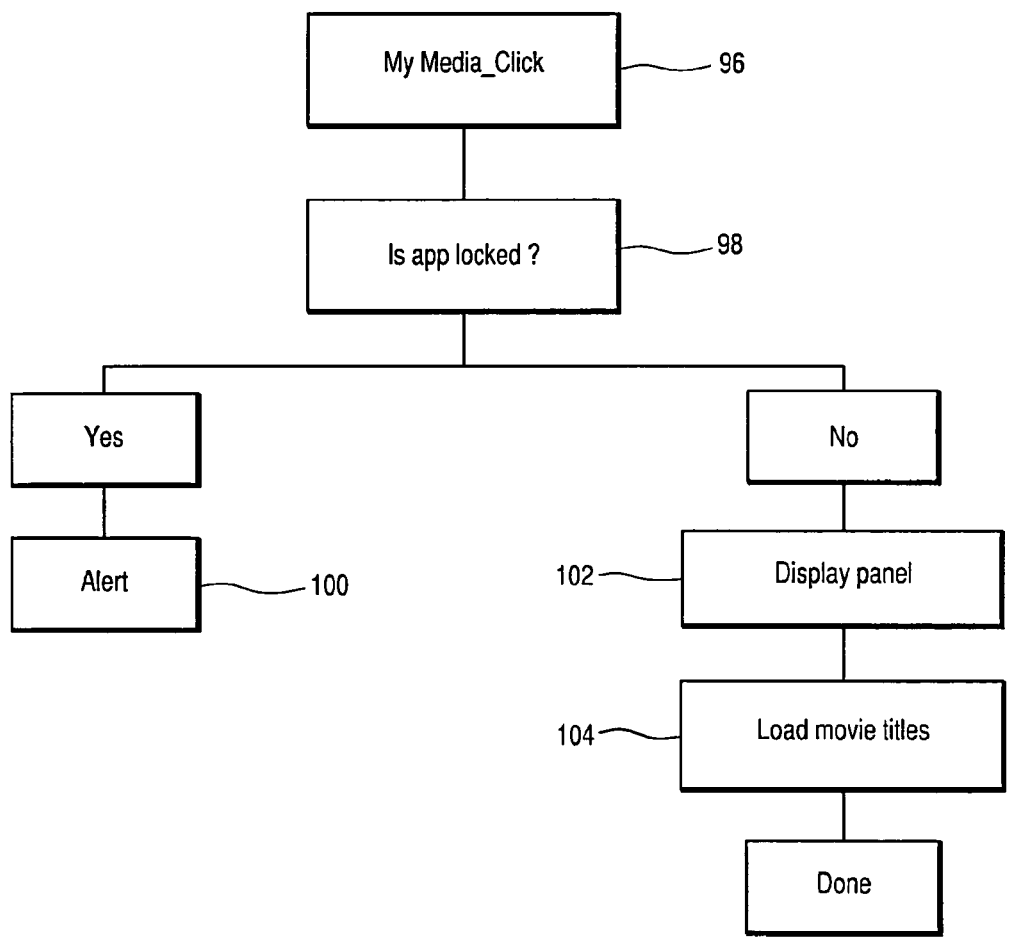
FIG. 16 is a flowchart showing the process when the "My Media" button on the touch screen display is pressed.
Figure 17:
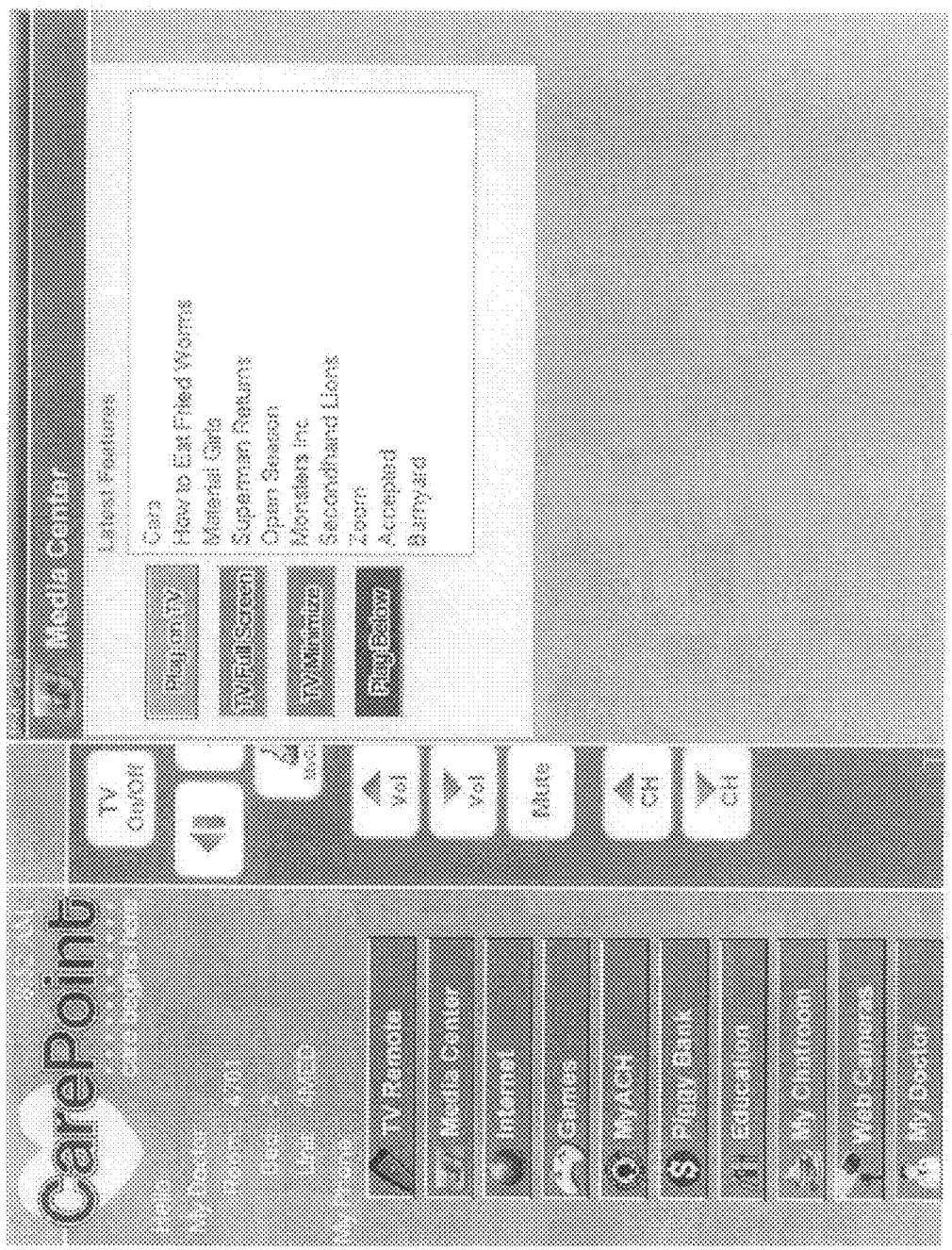
FIGS. 17 and 18 are sample screenshots of a display when the "My Media" button on the touch screen display is pressed.
Figure 18:
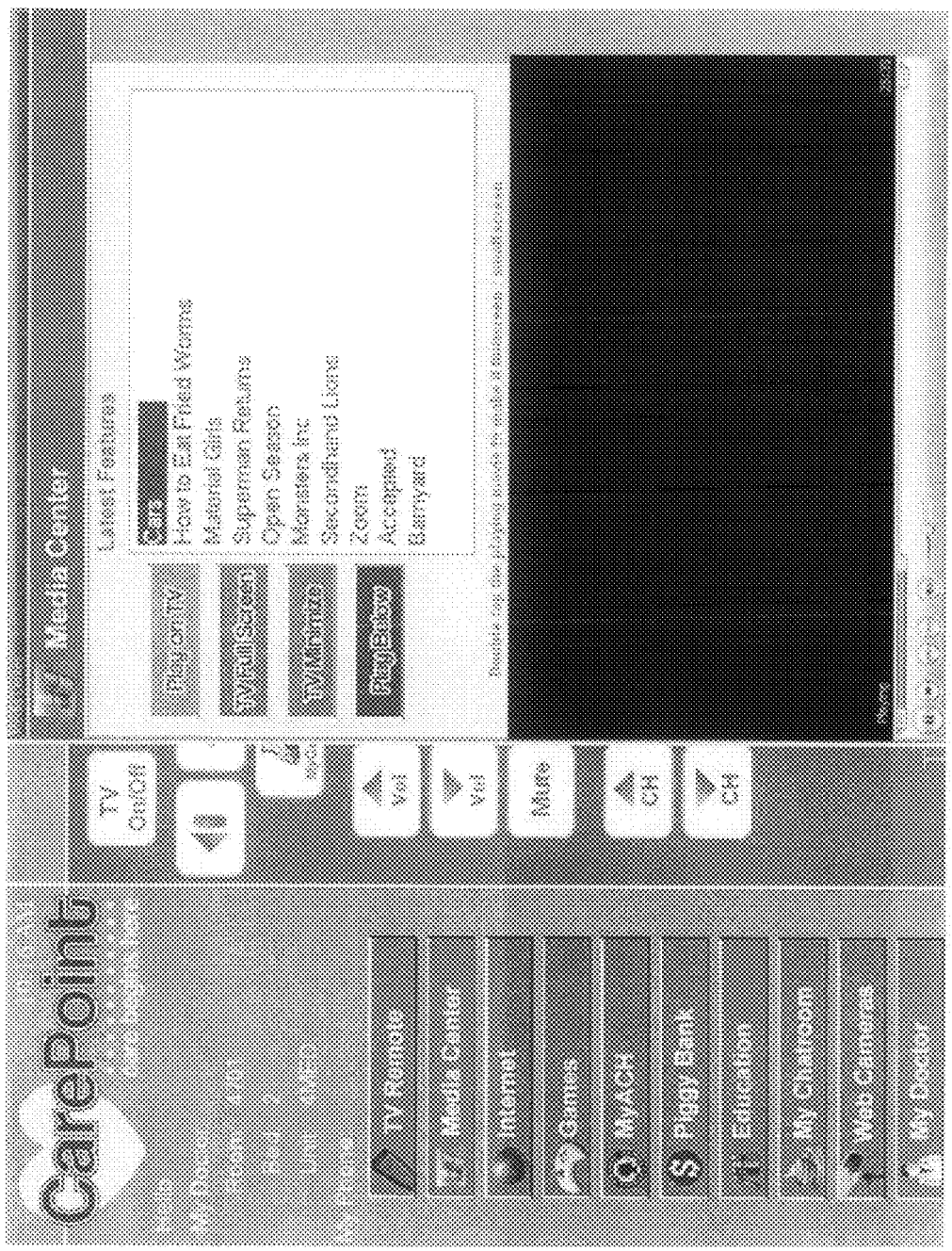

Referring to FIG. 14, when a patient presses the "My Chatroom" button 46 (FIG. 3) on the touch screen 12, the system initially checks the PC settings at 80 that were loaded when the system started to verify that a patient is currently in the room. If there is no patient, the system displays a message at 82 that says the function requested is not available. If a patient is listed in the room, the system begins the chat process, checking the settings to see if the chat function has been disabled at 84 by a guardian or a nurse (see Form Timer Functions). If the chat function has been disabled, the system displays a message at 86 saying that the function is not available. If it has not been disabled, the system begins a series of checks in the database in the server 51, determining She last chat room the patient used at 88 (Entire Hospital, Current Unit or Parent Portal), the last status at 90 (online or offline) and loads that status, loads a list of current chat users 92 (patients who are not listed as offline) based on the last chat room setting. The system then displays the chat form at 94, based on the information obtained initially. Examples of a My Chartroom screenshot display is shown in FIG. 15. The "chat" functionality includes the parent/guardian's ability to specifically identify family members and friends who have permission to communicate with the patient via the text-based "chat" system Referring to FIG. 16, when the patient presses the "My Media" button 34 (FIG. 3) at 96, the system will check at 98 the PC setting to see if there really is a patient in the room. If there is not, the system will display a message at 100 that the system is locked. If there is a patient listed for the room, the local settings will be checked to see if the My Media function has been disabled by a parent or nurse. If access has been disabled, the appropriate message is displayed at 102. If access is enabled, the system displays at 104 movie selections available, as shown, for example in a screenshot display in FIG. 17. This data comes from a server 51. When a patient touches a movie link on the screen, the system will give the option to view the movie on the touch screen 12 or on the monitor 16. When that selection is made, the movie begins to play from the PC 10 in the room. The system previously transfers the video files from the server 4 to the PC 10 when the Patient is admitted, to reduce the load on the hospital network. FIG. 18 shows the movie playing on the touch screen display 12.

Figure 19:
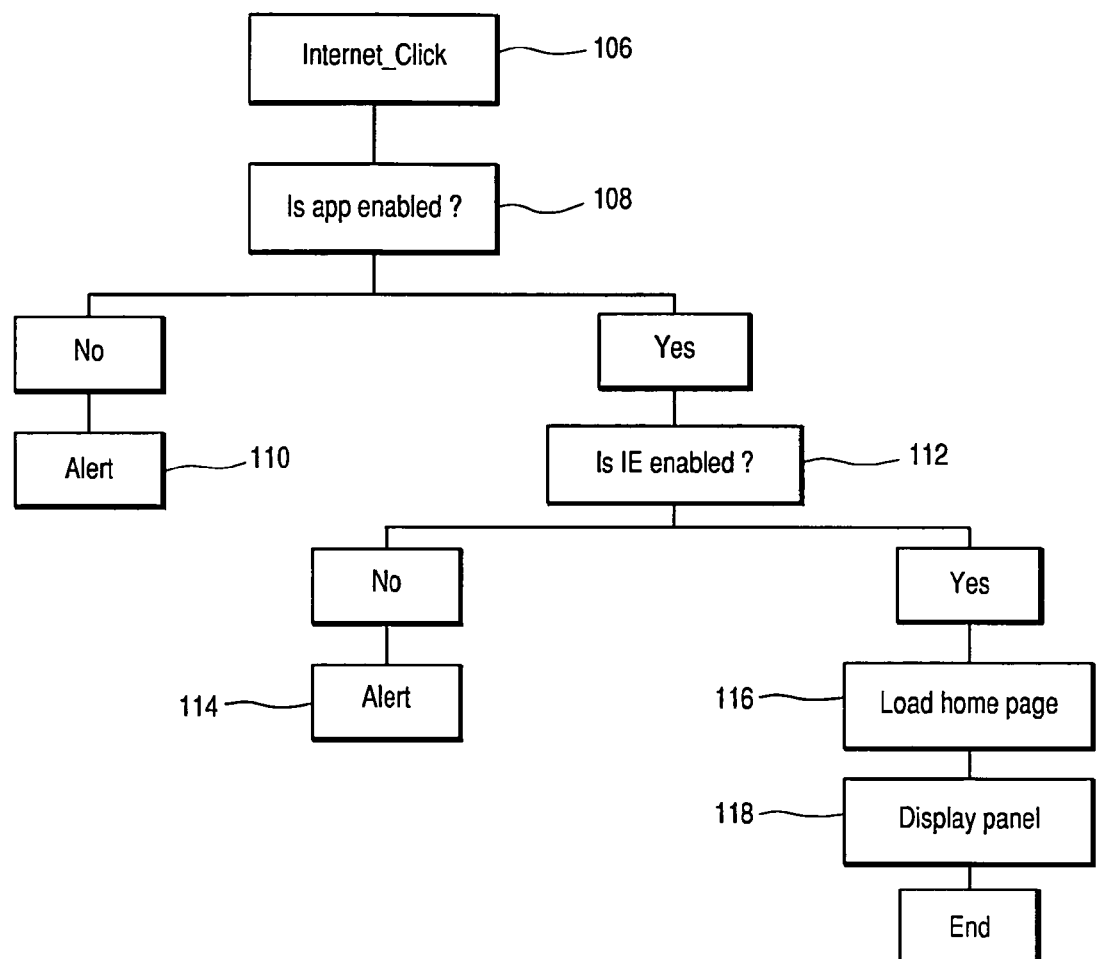
FIG. 19 is a flowchart showing the process when the "Internet" button on the touch screen display is pressed.
Figure 20:
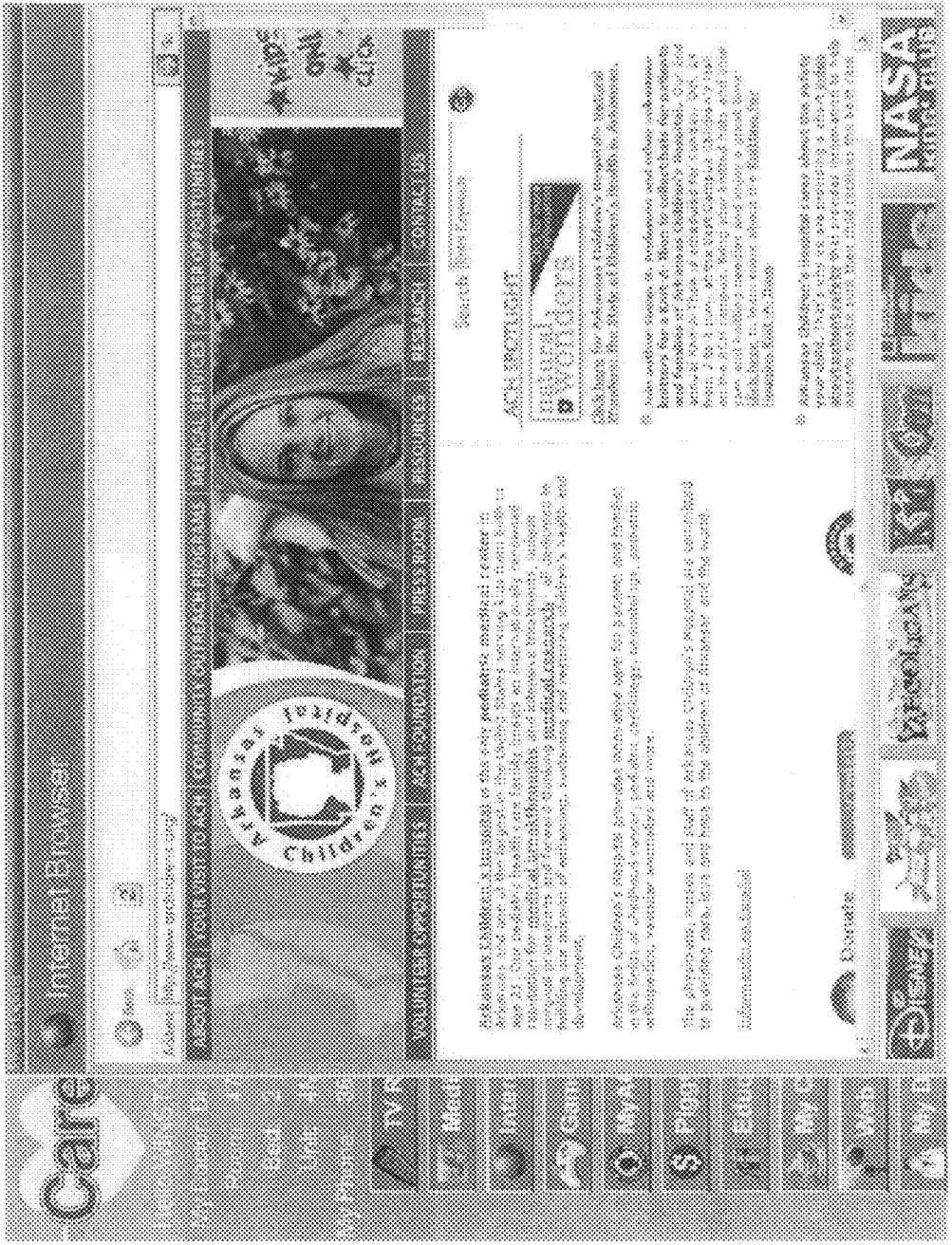
FIG. 20 is a sample screenshot of a display when the "Internet" button on the touch screen display is pressed.

Referring to FIG. 19, when a patient presses the "internet" button 36 (FIG. 3) at 106, the system will check the PC setting to see if there really is a patient in the room at 108. If there is not, the system will display a message that the system is locked at 110. If there is a patient listed for the room, the local settings will be checked to see if the internet access has been disabled by a parent or nurse at 112. If it has been disabled, the appropriate message is displayed at 114. If it is enabled, the system loads up a default home page at 116, opens a panel at 118 to display it in a web browser. An example of a screenshot display of the internet browser page is shown in FIG. 20.

Figure 21:
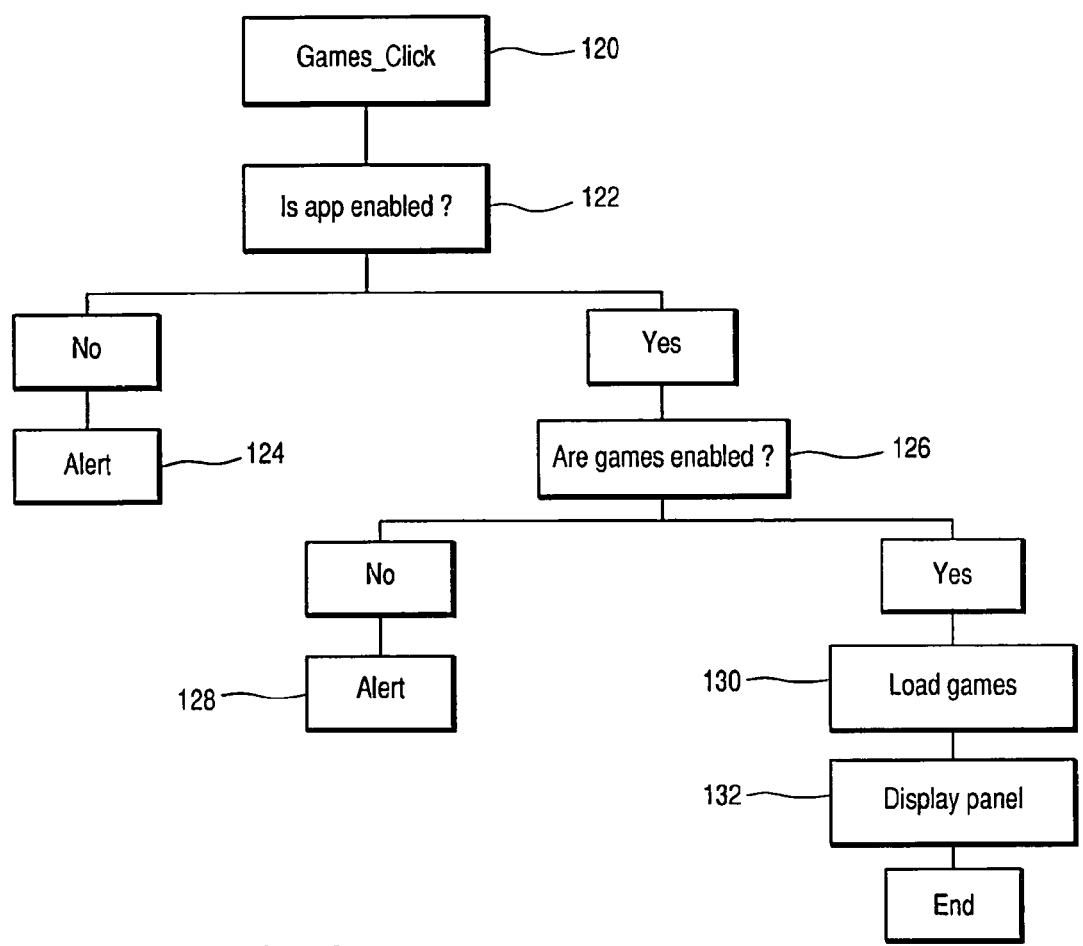
FIG. 21 is a flowchart showing the process when the "Games" button on the touch screen display is pressed.
Figure 22:
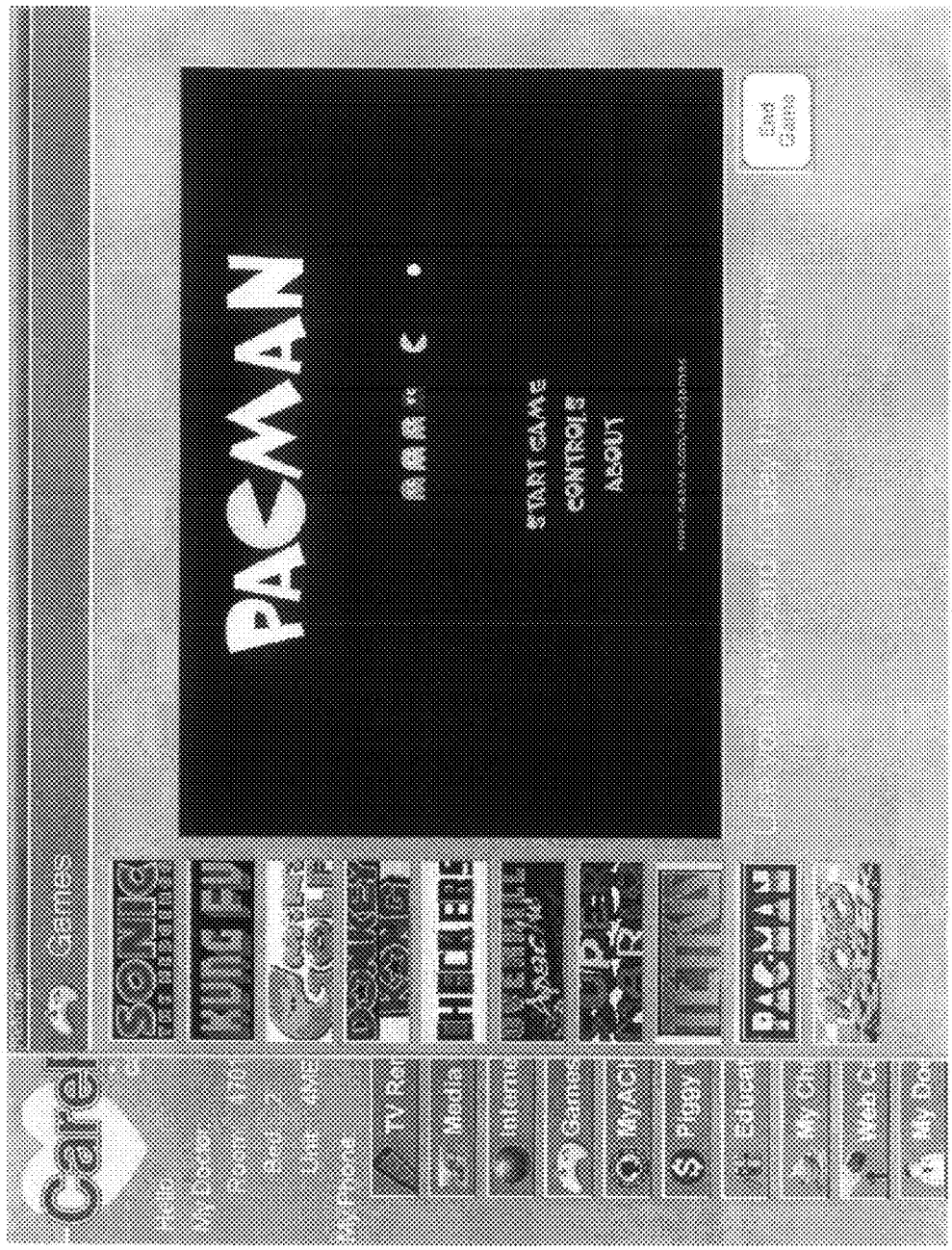
FIG. 22 is a sample screenshot of a display when the "Games" button on the touch screen display is pressed.

Referring to FIG. 21, when the "Games" button 38 (FIG. 3) is touched at 120, the system will check the PC settings at 122 to see if there really is a patient in the room. If there is not, the system will display a message at 124 that the system is locked. If there is a patient listed for the room, the local settings will be checked to see if the games have been disabled at 126 by a parent or nurse. If they have been disabled, the appropriate message is displayed 128. If they are enabled, the system loads the file paths to the various games at 130 and loads the graphic display form at 132. When a patient touches a game link on the screen, the system runs the appropriate game file. An example of a screenshot display showing the various game links available to the patient is shown in FIG. 22.

Figure 23:
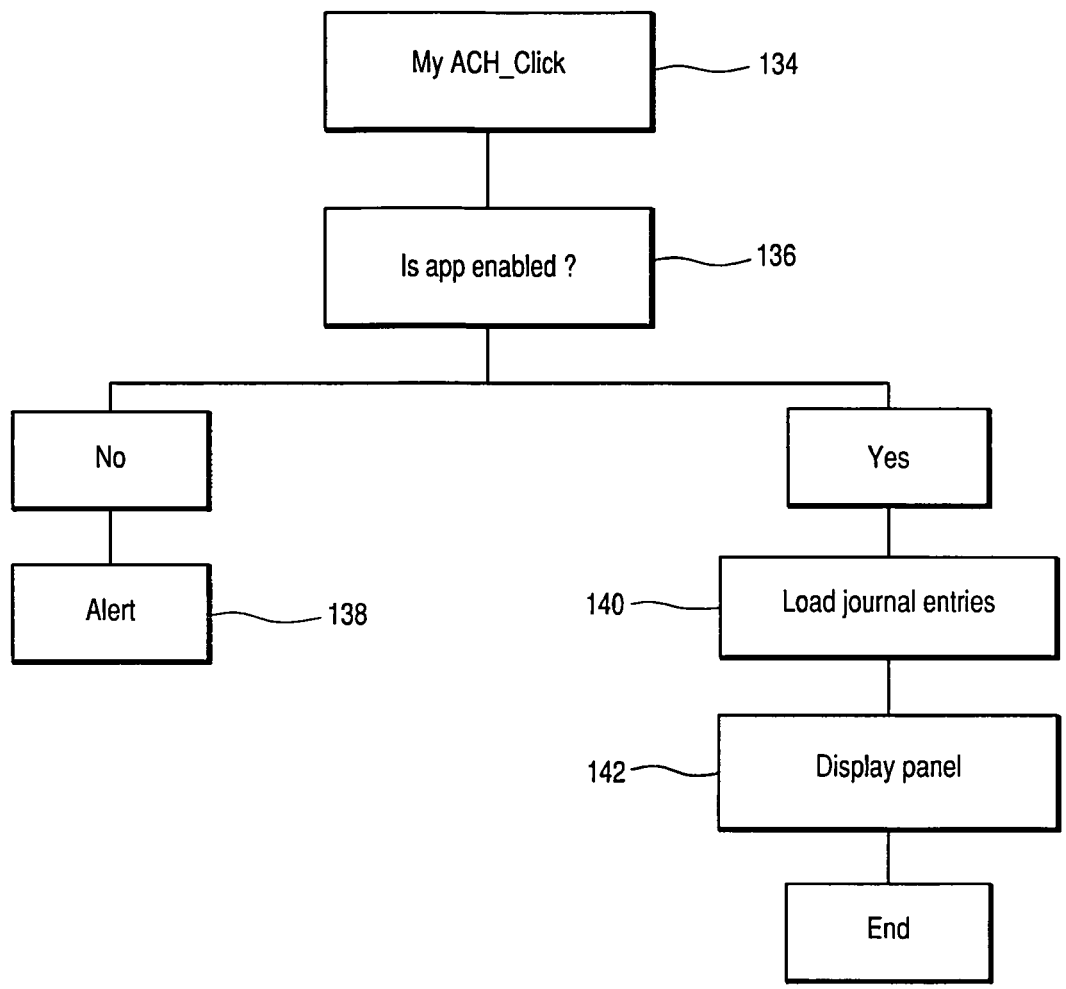
FIG. 23 is a flowchart showing the process when the "My ACH" button on the touch screen display is pressed.
Figure 24:
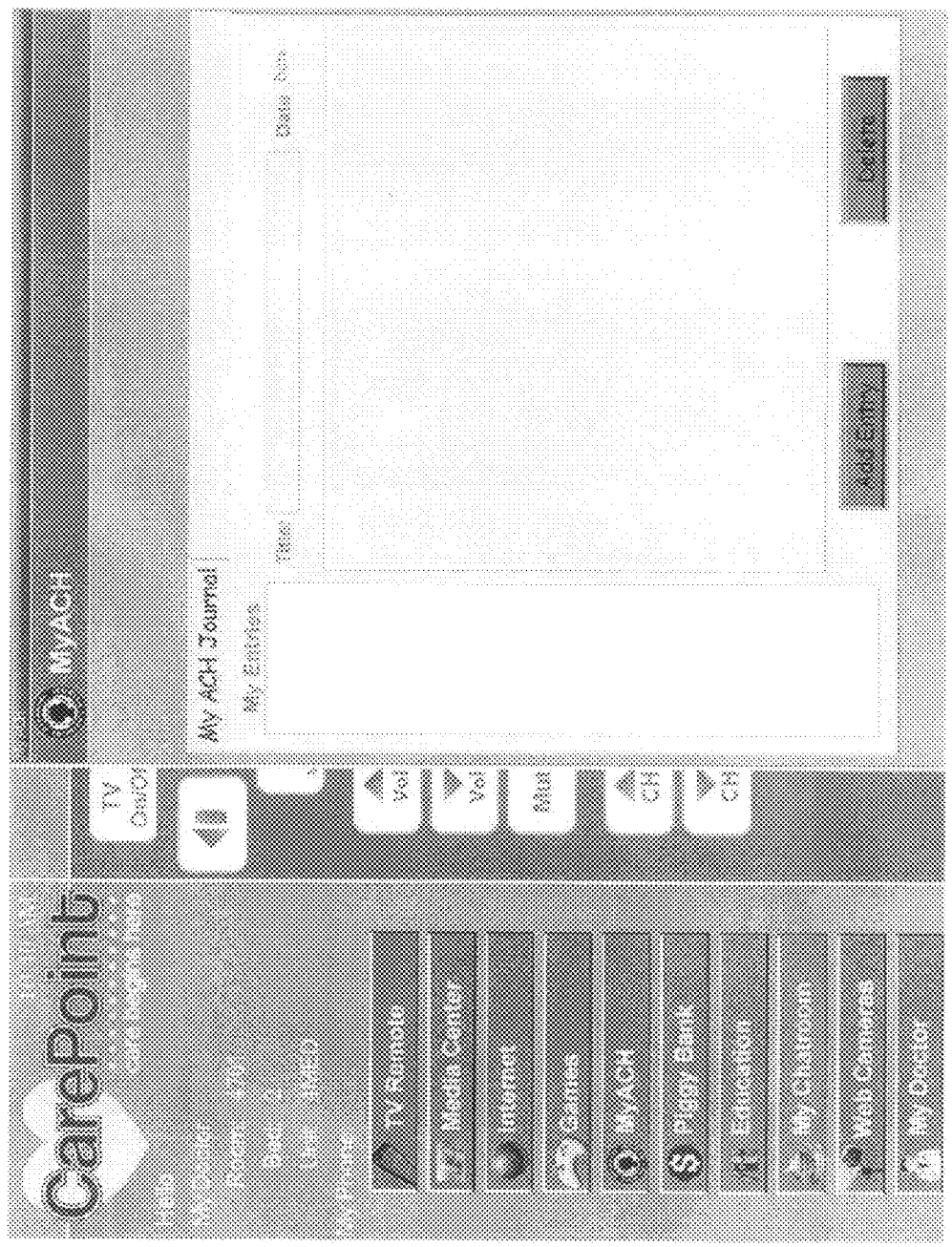
FIG. 24 is a sample screenshot of a display when the "My ACH" button on the touch screen display is pressed.

Referring to FIG. 23, when the "My ACH" button 40 (FIG. 3) is touched at 134, the system will check the PC setting at 136 to see if there really is a patient in the room. If there is not, the system will display a message at 138 that the system is locked. If there is a patient listed for the room, the system retrieves the patient's journal entries at 140 from the server 51 and displays a list of dates at 142. When a date is selected, the system retrieves the specific entry from the server 51 and displays it. FIG. 24 shows an example of a screenshot display of the MyAch functionality.

Figure 25:
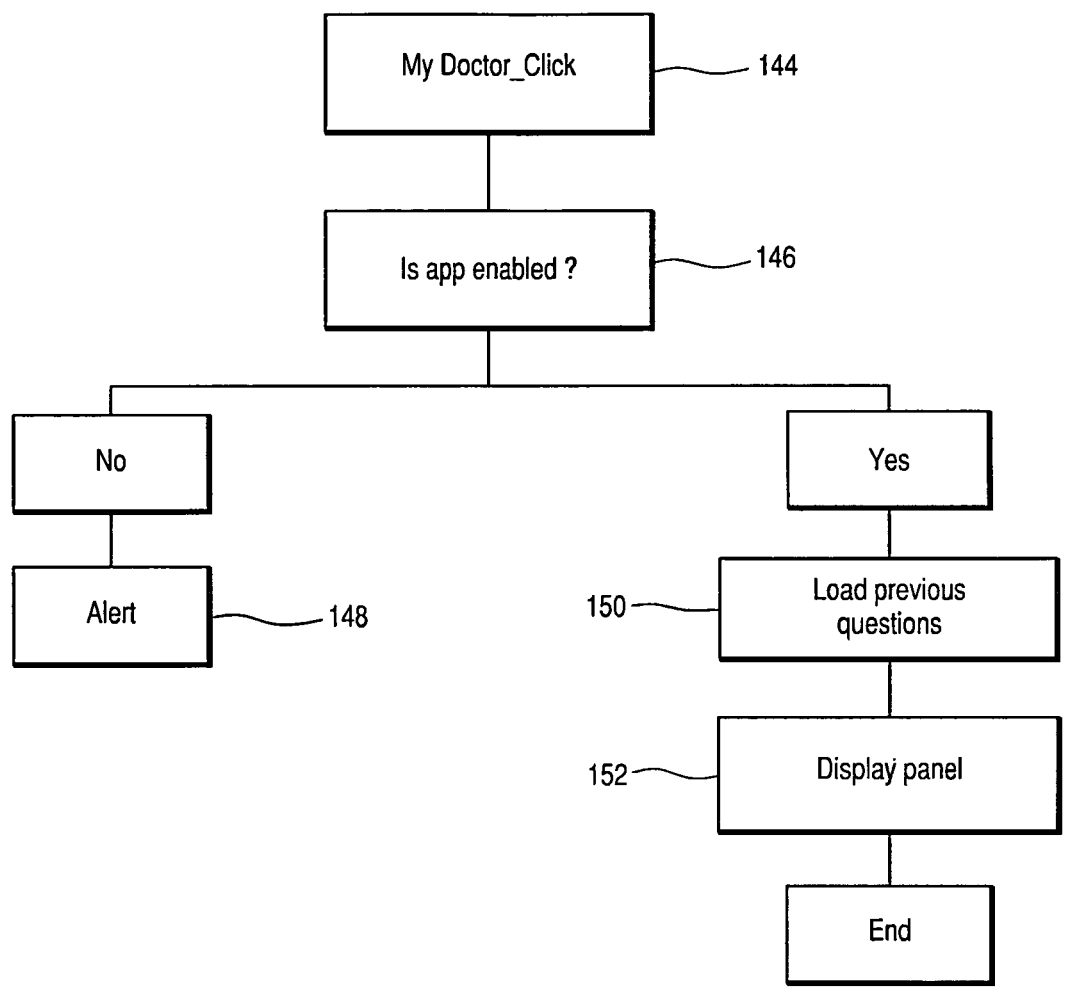
FIG. 25 is a flowchart showing the process when the "My Doctor" button on the touch screen display is pressed.
Figure 26:
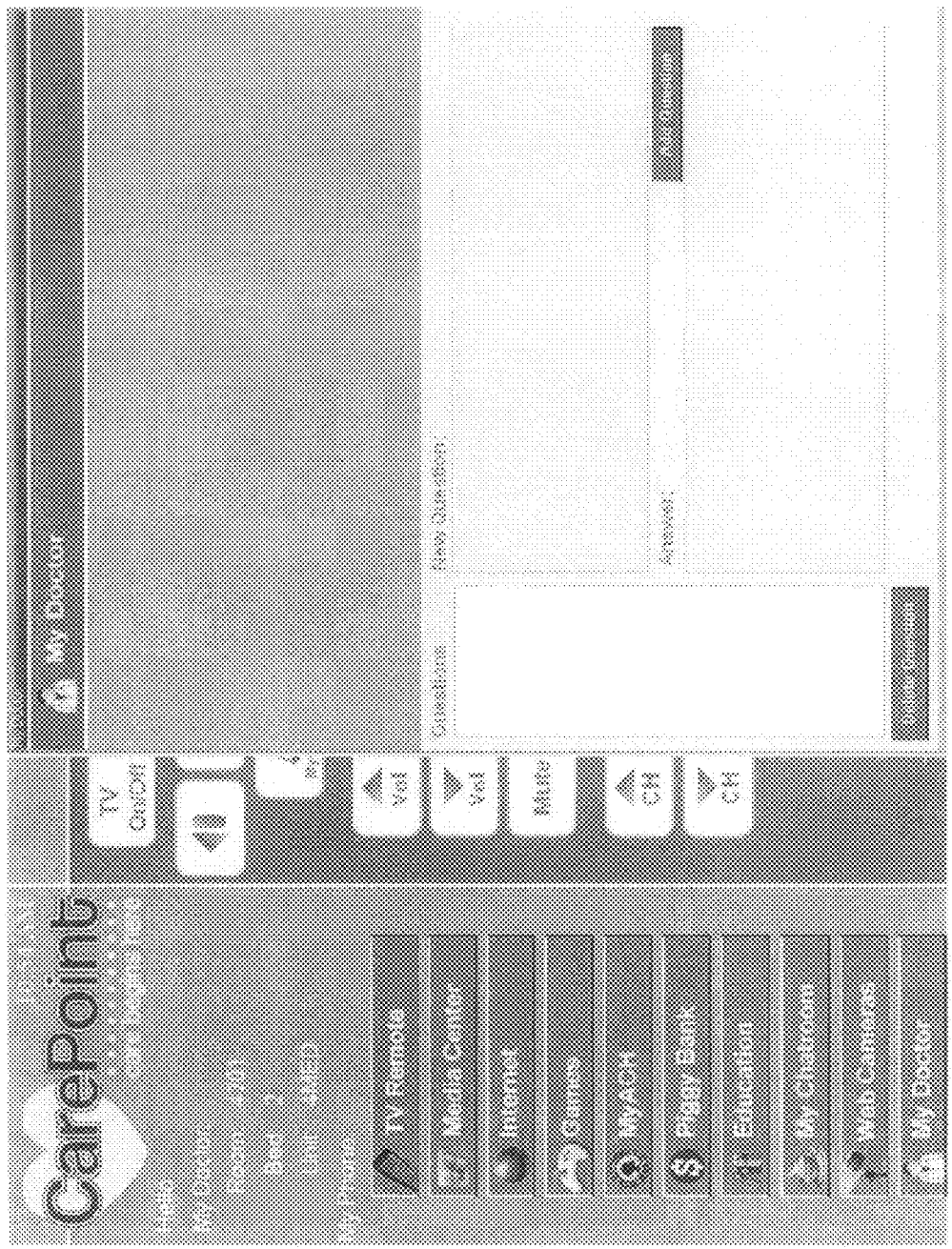
FIG. 26 is a sample screenshot of a display when the "My Doctor" button on the touch screen display is pressed.

Referring to FIG. 25, when the "My Doctor" button 50 (FIG. 3) is touched at 144, the system will check the PC setting at 146 to see if there really is a patient in the room. If there is not, the system will display a message at 148 that the system is locked. If there is a patient listed for the room, the system retrieves at 150 all previous entries from the server 51 and displays a list of dates at 152. When a date is selected, the system retrieves the specific entry from the server 51 and displays it. This function is used by the patients to leave questions for their doctor, to be addressed during the next visit by the physician. FIG. 26 shows an example of a screenshot display of the My Doctor functionality.

Figure 27:
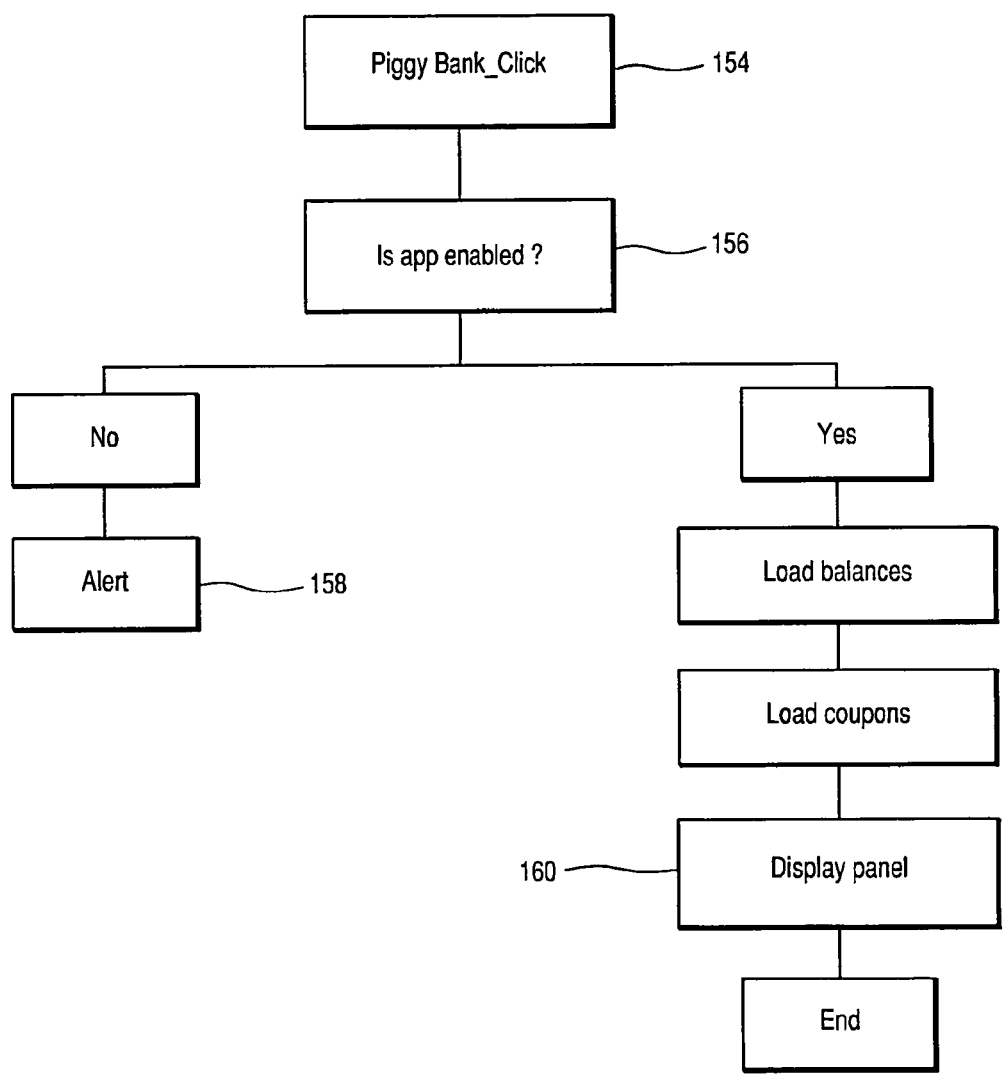
FIG. 27 is a flowchart showing the process when the Piggy Bank button on the touch screen display is pressed.
Figure 28:
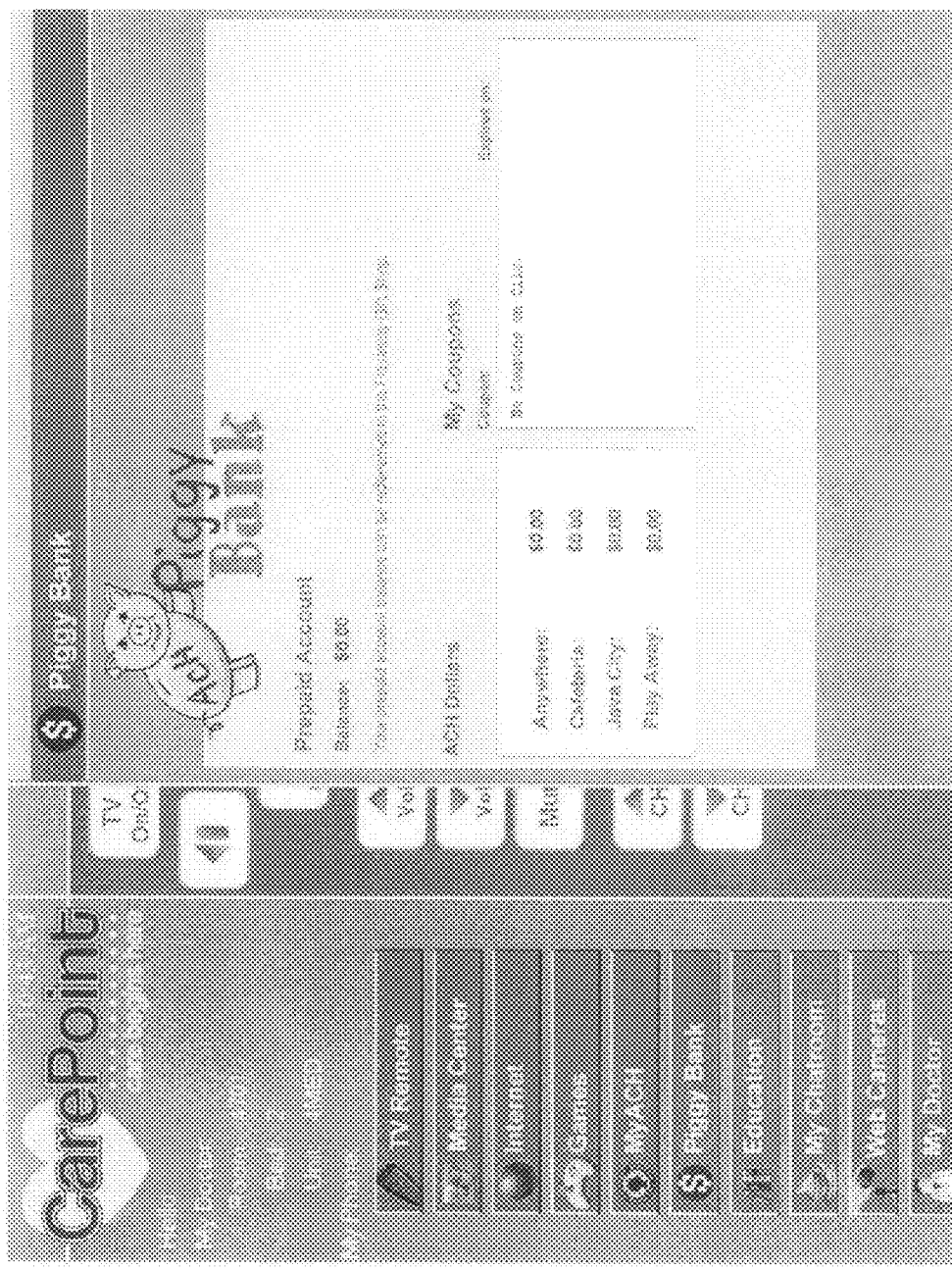
FIG. 28 is a sample screenshot of a display when the "Piggy Bank" button on the touch screen display is pressed.

Referring to FIG. 27, when the "Piggy Bank" button 42 (FIG. 3) is touched at 154, the system will check the PC setting at 156 to see if there really is a patient in the room. If there is not, the system will display a message at 158 that the system is locked. If there is a patient listed for the room, the appropriate account balance and coupon information will be accessed from the server 51 and displayed at 160. FIG. 28 is an example of a screenshot display of the Piggy Bank functionality.

Figure 29:
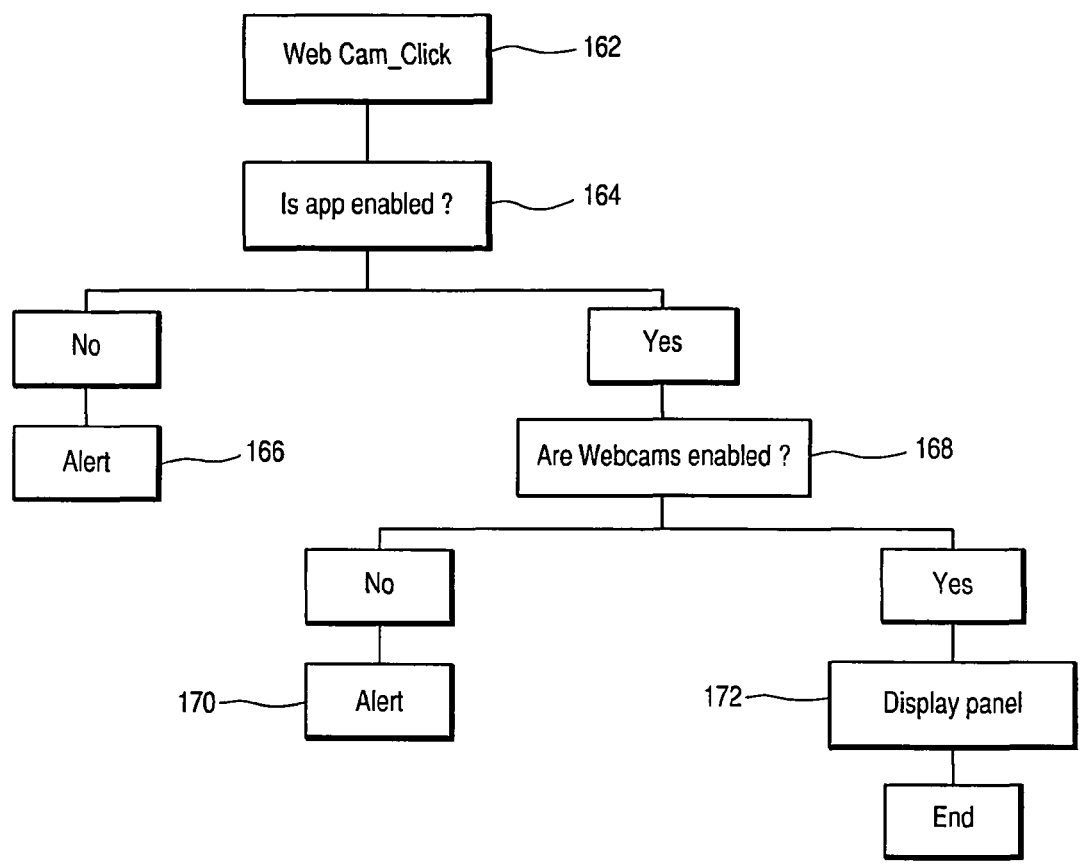
FIG. 29 is a flowchart showing the process when the "Web Cameras" button on the touch screen display is pressed.

Referring to FIG. 29, when the "Web Cameras" button 48 (FIG. 3) is touched at 162, the system will check the PC setting at 164 to see if there really is a patient in the room. If there is not, the system will display a message that the system is locked at 166. If there is a patient listed for the room, the local settings will be checked at 168 to see if the webcams have been disabled by a parent or nurse. If they have been disabled, the appropriate message is displayed at 170. If they are enabled, the system displays a form at 172 listing the webcams. When a patient touches a webcam link on the screen, the system accesses the appropriate webcam feed.

Music upload through web portal 53 is done in the following manner. The user logs into the web portal 53, for example from the remote, using a secure username and password. The system checks that access information against the database in the server 51. If access fails, the system displays a message and the user can enter the correct information. If access is granted, the system will display a list of patients associated with their account. That information comes from the database in the server 51. The user selects a patient and the system will display a list all available options, including music upload. If the user selects that function, the system displays a "music upload form". As that form is loading, the system accesses, from a database in the server 51, a list of all songs that have been uploaded for the specific patient. If the user wants to upload a new audio file, the "upload" button on the form is selected. The system allows 20 songs to be uploaded, for example. When the "upload" button is clicked, the system first checks to make sure the maximum count has not been reached. If it has, the system displays a message indicating the song limit has been reached. If the limit has not been reached, the system displays a file browser that allows the user to find the music file on its computer. Once the file is found, the system checks the file information. If the file is too large, the system displays a message to the user, notifying it that the file must be smaller than five megabytes. If the file meets system specifications, the transfer begins. The system creates a database record in the server 51 linking that particular file to the specified patient. That information is used to provide access to the file from the patient's touch screen 12. The system then refreshes the list displayed on the web portal page to reflect the new upload.

Figure 30:
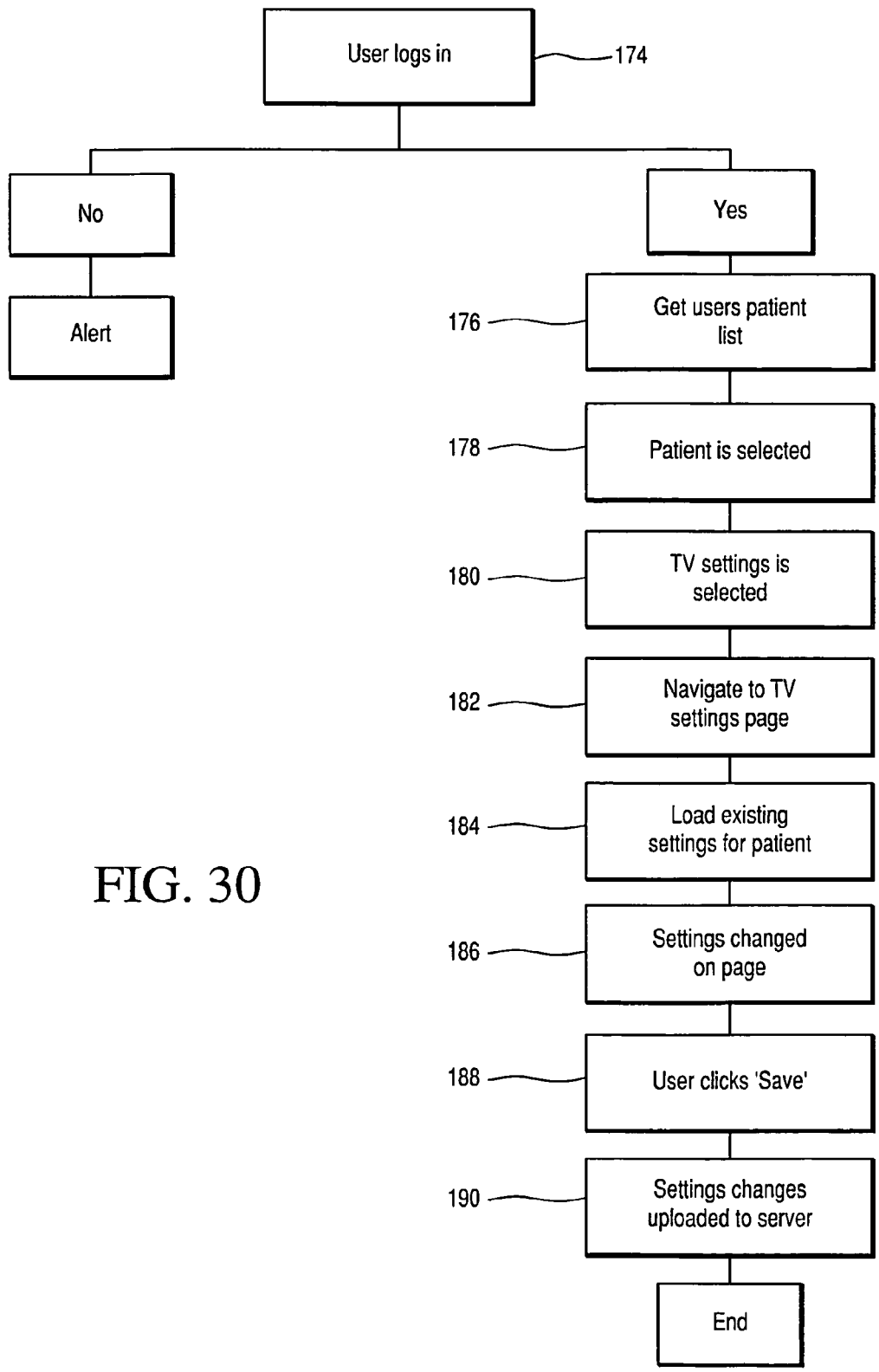
FIG. 30 is a flowchart showing the process of logging in through the Web portal to allow a parent or guardian to impose parental control to block certain TV channels that may not be appropriate for the patient to view.

Referring to FIG. 30, a parental control flowchart is disclosed that allows a parent or guardian to block certain TV channels that may not be appropriate for the patient to view by making changes to the system options through the web portal 53. The user logs into the system at 174, using a username and password. When the system recognizes the user, the user is presented with a list of patients at 176 that the system knows the user is a guardian for. The user selects the patient needed at 178 and is presented with a list of system options. The user selects the TV Settings option at 180 and the system navigates to the TV Settings page at 182. The system loads the existing settings at 184 for that patient from the server 51. The user makes desired changes at 186 and clicks "save" at 188. The system stores the changed options on the server 51 at 190. The PC 10 polls the server 51 every few minutes, looking for changes.

Figure 31:
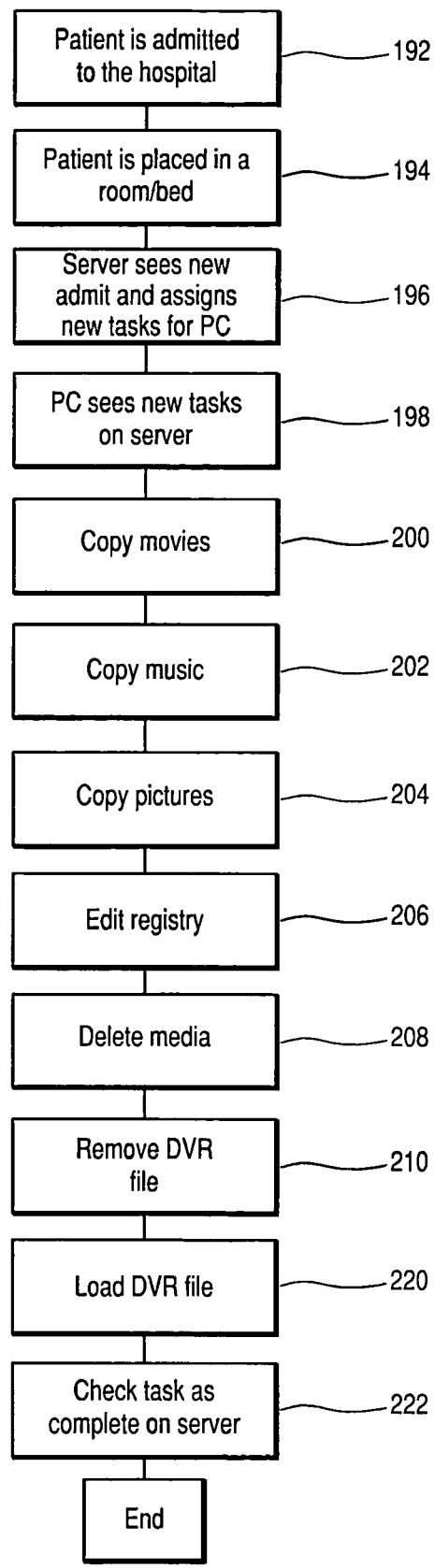
FIG. 31 is a flowchart showing the process for setting up the room computer for a specific patient.

Referring to FIG. 31, a flowchart is disclosed that sets up the PC 10 for a specific patient. When the patient is admitted to the hospital at 192, the patient is admitted to a specific unit, room and bed at 194. Within minutes, the Current Patient Database in the server 51 picks up the new admission and assigns a series of tasks for the PC 10 at 196 associated with that unit, room and bed. The PC 10 is checking for new tasks every minute or two, polling the server 51 for a list of tasks at 198. The first task is to copy age-specific movies from the server 51 to the PC 10 at 200. The system then does the same thing with music and pictures at 202 and 204. The next task is to edit the registry on the PC to 10 at 206 to specify the appropriate television viewing level, based on the age of the patient. The system then deletes at 208 any media currently on the PC 10 that do not meet age specifications. The system then removes the DVR file at 210 currently on the PC 10 (this file contains information on upcoming recordings scheduled by the previous patient). The system then checks the server 51 for a DVR file with preferences and load those preferences at 220 (this file contains information about preferences from previous hospital visits or from an earlier room assignment). The system then reports back to the server 51 that all tasks have been completed at 222.

Software used in the system 2 includes Microsoft ASP-.NET, Microsoft SQL Server 2005, Microsoft Visual Studio 2005, Microsoft Visual Studio 2005 Team Foundation Server and Microsoft Windows XP Professional.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

I claim:

1. A patient hospital room system, comprising:
   a) a room computer uniquely associated with a patient in a hospital room, said room computer is connected to a hospital network including a media server, said media server is configured to receive preselected media files uploaded by a patient prior to being admitted, said room computer is configured to automatically download said preselected media files from said media server when the patient is assigned to the room;
   b) a touch screen display operably connected to said room computer, said room computer is configured to enable said touch screen display to function as a remote controller for playing said media files;
   c) a game console operably connected to said room computer;
   d) a monitor connected to said game console;
   e) an IR transmitter connected to said room computer for transmitting commands from said touch screen display to said game console;
   f) an IR receiver operably connected to said game console for receiving said commands from said IR transmitter; and
   g) said room computer and said game console are configured such that said preselected media files are playable from said room computer and displayable on said touch screen or said monitor.

2. A patient hospital room system as in claim 1, and further comprising:
   a) a database server; and
   b) said room computer is configured to periodically poll said database server for tasks to perform.

3. A patient hospital room system as in claim 2, wherein said tasks include copying movie files.

4. A patient hospital room system as in claim 2, wherein said tasks include copying music files.

5. A patient hospital room system as in claim 2, wherein said tasks include copying pictures.

6. A patient hospital room system as in claim 2, wherein said database server is configured for generating tasks for said room computer when a patient is admitted to the hospital room.

7. A patient hospital room system as in claim 6, and further comprising:
   a) a TV source connected to said room computer; and
   b) said web portal is configured for accepting and saving instructions on said database server for limiting selected TV channels to be provided for viewing by the patient in the room.

8. A patient hospital room system as in claim 1, and further comprising an administrative computer configured to turn on or off said room computer and said game console.

9. A patient hospital room system as in claim 1, and further comprising a card reader operably connected to said room computer for gaining access to the patient's medical records.

10. A patient hospital room system as in claim 9, wherein said room computer is configured for limiting access to the patient's medical records to only those assigned to the patient.

11. A patient hospital room as in claim 1, wherein said media files are uploaded into said media server prior to the patient being admitted.

12. A patient hospital room system as in claim 1, wherein said computer is located on a wall behind the patient.

13. A patient hospital room system as in claim 12, wherein said monitor is disposed on a wall opposite said room computer.

14. A patient hospital room system as in claim 1, wherein said touch screen display is supported on a movable arm.

15. A patient hospital room system as in claim 1, and further comprising a web portal accessible by a user from a remote location for uploading media files to said media server for copying to said room computer.

16. A patient hospital room system, comprising:
    a) a room computer uniquely associated with a patient in a hospital room, said room computer is connected to a hospital network including a database server, said room computer is configured to periodically check for and load setting options stored in said database server;
    b) a touch screen display operably connected to said room computer, said room computer is configured to enable said touch screen display to function as a remote controller;
    c) a game console operably connected to said room computer;
    d) a monitor connected to said game console;
    e) an IR transmitter connected to said room computer for transmitting commands from said touch screen display to said game console; and
    f) an IR receiver operably connected to said game console for receiving said commands from said IR transmitter.

17. A patient hospital room system as in claim 16, wherein said room computer is configured to perform tasks listed by said database server when a patient is assigned to the hospital room.

18. A patient hospital room system as in claim 16, wherein:
    a) said touch screen display includes a number of function buttons; and
    b) said room computer is configured to check if a patient is assigned to the room when a function button is pressed.

19. A patient hospital room system as in claim 16, wherein:
    a) said touch screen display includes an "Education" button; and
    b) said room computer is configured to display available educational video titles related to the patient's diagnosis when said "Education" button is pressed and to play a selected title.

20. A patient hospital room system as in claim 16, wherein said room computer is configured to allow the patient to send a written message to a doctor assigned to the patient.

21. A patient hospital room system as in claim 16, wherein said room computer is configured to provide access to the Internet.

22. A patient hospital room system as in claim 16, wherein:
    a) said touch screen display includes a "Games" button; and
    b) said room computer is configured check if the patient is allowed to play games when said "Games" button is pressed.

23. A patient hospital room system as in claim 16, wherein:
    a) said touch screen display includes a "Media Center" button; and
    b) said room computer is configured to display movie titles when said "Media Center" button is pressed and to play a selected title on said touch screen display or said monitor display.

24. A patient hospital room system, comprising:
    a) a room computer uniquely associated with a patient in a hospital room, said room computer is automatically loaded with appropriate content from a server connected to said room computer as soon as the patient is assigned to a room;
b) a touch screen display operably connected to said room computer, said touch screen display including a plurality of buttons, each one corresponding to a command when pressed;
c) said room computer is configured to create a text file corresponding to a button pressed on said touch screen display, read said text file and initiate said command;
d) a game console operably connected to said room computer;
e) a monitor connected to said game console;
f) an IR transmitter connected to said room computer for transmitting said command from said touch screen display to said game console; and
g) an IR receiver operably connected to said game console for receiving said commands from said IR transmitter.

25. A patient hospital room system as in claim 24, wherein said game console is operably connected to said room computer through said hospital network.

\* \* \* \* \*